(12) United States Patent
Sullivan

(10) Patent No.: US 9,538,931 B2
(45) Date of Patent: Jan. 10, 2017

(54) REDUCING ELECTROCARDIOGRAM ARTIFACTS DURING AND POST CPR

(71) Applicant: Physio-Control, Inc., Redmond, WA (US)

(72) Inventor: Joseph L Sullivan, Kirkland, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

(21) Appl. No.: 14/595,119

(22) Filed: Jan. 12, 2015

(65) Prior Publication Data

US 2015/0313493 A1 Nov. 5, 2015

Related U.S. Application Data

(63) Continuation-in-part of application No. 13/676,593, filed on Nov. 14, 2012, now Pat. No. 9,084,545.
(Continued)

(51) Int. Cl.
| | |
|---|---|
| *A61B 5/05* | (2006.01) |
| *A61B 5/04* | (2006.01) |
| *A61B 5/053* | (2006.01) |
| *A61B 5/00* | (2006.01) |
| *A61N 1/39* | (2006.01) |
| *A61B 5/046* | (2006.01) |
| *A61H 31/00* | (2006.01) |

(52) U.S. Cl.
CPC ........... *A61B 5/04017* (2013.01); *A61B 5/046* (2013.01); *A61B 5/053* (2013.01); *A61B 5/7217* (2013.01); *A61H 31/005* (2013.01); *A61H 31/006* (2013.01); *A61N 1/3925* (2013.01); *A61H 2201/0103* (2013.01); *A61H 2201/5007* (2013.01); *A61H 2201/5043* (2013.01); *A61H 2201/5071* (2013.01); *A61H 2201/5097* (2013.01); *A61H 2230/045* (2013.01); *A61H 2230/206* (2013.01); *A61H 2230/208* (2013.01); *A61H 2230/305* (2013.01)

(58) Field of Classification Search
CPC ................. A61H 2031/025; A61H 2201/1238; A61H 2201/165; A61N 1/39
See application file for complete search history.

(56) References Cited

U.S. PATENT DOCUMENTS 4,422,459 A * 12/1983 Simson ......................... 600/515
5,687,735 A    11/1997 Forbes et al.
(Continued)

FOREIGN PATENT DOCUMENTS

WO        2009071128        6/2009

OTHER PUBLICATIONS

Dotsinsky, I., Suppression of AC railway power-line interference in ECG signals recorded by public access defibrillators, BioMedical Engineering Online (2005) 4:65.
(Continued)

*Primary Examiner* — Rex R Holmes
(74) *Attorney, Agent, or Firm* — Marger Johnson

(57) ABSTRACT

A portable medical device having improved ECG trace display and reporting. Embodiments implement features to ameliorate artifacts created by virtue of attempting to eliminate compression artifacts due to mechanical compression devices. Other embodiments additionally implement features to seek to detect the occurrence of ROSC while chest compressions are ongoing.

12 Claims, 23 Drawing Sheets

DEFIBRILLATION SCENE

Related U.S. Application Data

(60) Provisional application No. 61/926,176, filed on Jan. 10, 2014, provisional application No. 61/616,874, filed on Mar. 28, 2012, provisional application No. 61/616,727, filed on Mar. 28, 2012, provisional application No. 61/616,973, filed on Mar. 28, 2012, provisional application No. 61/616,660, filed on Mar. 28, 2012, provisional application No. 61/616,372, filed on Mar. 27, 2012, provisional application No. 61/616,847, filed on Mar. 28, 2012.

(56) References Cited

U.S. PATENT DOCUMENTS

| | | |
|---|---|---|
| 6,752,771 B2 | 6/2004 | Rothman et al. |
| 7,039,457 B2 | 5/2006 | Young et al. |
| 7,220,235 B2 | 5/2007 | Geheb et al. |
| 7,565,194 B2 | 7/2009 | Tan et al. |
| 7,567,837 B2 | 7/2009 | Weil et al. |
| 7,650,181 B2 | 1/2010 | Freeman et al. |
| 7,831,299 B2 | 11/2010 | Tan et al. |
| 2002/0165471 A1 | 11/2002 | Halperin et al. |
| 2005/0101889 A1 | 5/2005 | Freeman et al. |
| 2005/0137628 A1 | 6/2005 | Young et al. |
| 2005/0256415 A1 | 11/2005 | Tan et al. |
| 2006/0025824 A1 | 2/2006 | Freeman et al. |
| 2006/0149157 A1 | 7/2006 | Weil et al. |
| 2006/0235320 A1 | 10/2006 | Tan et al. |
| 2006/0258927 A1 | 11/2006 | Edgar et al. |
| 2007/0100379 A1 | 5/2007 | Tan et al. |
| 2007/0162076 A1 | 7/2007 | Tan et al. |
| 2010/0076510 A1 | 3/2010 | Lyster |
| 2011/0034816 A1 | 2/2011 | Tan et al. |
| 2011/0105930 A1 | 5/2011 | Thiagarajan et al. |
| 2011/0202100 A1 | 8/2011 | Tan et al. |
| 2011/0202101 A1 | 8/2011 | Tan et al. |
| 2012/0010543 A1 | 1/2012 | Johnson et al. |
| 2012/0016279 A1 | 1/2012 | Banville et al. |
| 2012/0157865 A1 | 6/2012 | Stein et al. |
| 2013/0184600 A1* | 7/2013 | Tan et al. ............... 600/518 |
| 2014/0088374 A1 | 3/2014 | Sullivan et al. |

OTHER PUBLICATIONS

Dotsinsky, I. et al., Fast electrocardiogram amplifier recovery after a defibrillation shock, Bioautomation (2005) 2:76-84.

Ruiz, J. et al., Cardiopulmonary resuscitation artefact suppression using a Kalman filter and the frequency of chest compressions as the reference signal, Resuscitation 81 (2010) 1087-1094.

Aramendi et al., Detection of ventricular fibrillation in the presence of cardiopulmonary resuscitation artefacts, Resuscitation (2007) 75: 115-123.

Lee, B. et al., Adaptive comb filtering for motion artifact reduction from PPG with a structure of adaptive lattice IIR notch filter, 33rd Annual International Conference of the IEEE EMBS, Boston, MA, Aug. 30-Sep. 3, 2011, 4 pages.

Granegger, M. et al., Use of independent component analysis for reducing CPR artefacts in human emergency ECGs, Resuscitation (2011) 82: 79-84.

Irusta U. et al., A least mean-square filter for the estimation of the cardiopulmonary resuscitation artifact based on the frequency of the compressions, IEEE Trans Biomed Eng (2009) 56:21052-62.

Ruiz de Gauna et al., A method to remove CPR artefacts from human ECG using only the recorded ECG, Resuscitation (2008) 76, 271-278.

Aramendi et al., Suppression of the cardiopulmonary resuscitation artefacts using the instantaneous chest compressions rate extracted from the thoracic impedance, Resuscitation 83 (2012) 692-698.

Berger et al., Rhythm discrimination during uninterrupted CPR using motion artifact reduction system, Resuscitation (2007) 75, 145-152.

Aramendi, et al., "A simple effective filtering method for removing CPR cause artefacts from surface ECG signals"; Computers in Cardiology; 2005; pp. 547-550.

International Search Report and Written Opinion; Patent Cooperation Treaty; Oct. 1, 2013; 22 pages; PCT/US2013/039555, European Patent Office.

* cited by examiner

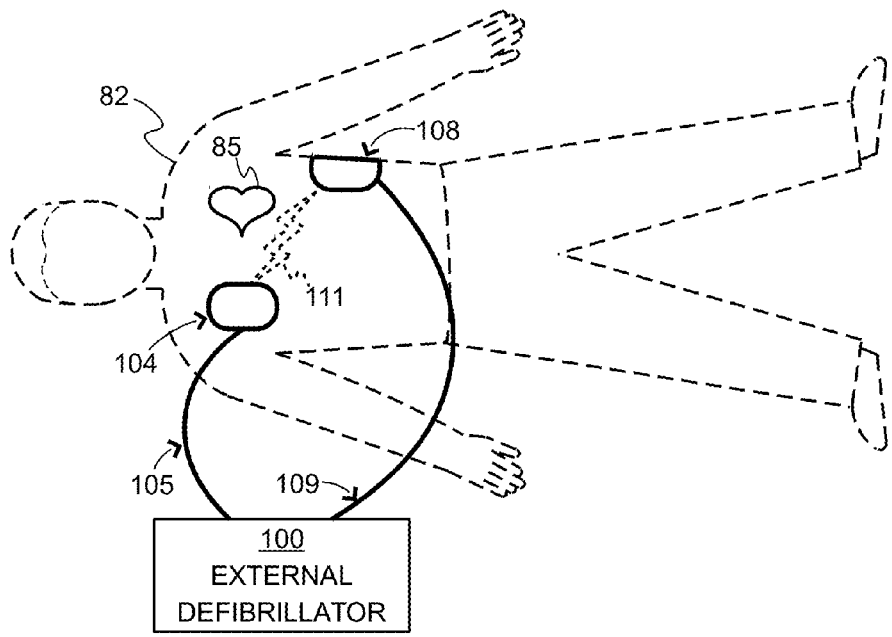
FIG. 1  *DEFIBRILLATION SCENE*
| TYPE OF EXTERNAL DEFIBRILLATOR | INTENDED TO BE USED BY PERSONS: ||
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2  *TWO MAIN TYPES OF EXTERNAL DEFIBRILLATORS*

COMPONENTS OF EXTERNAL DEFIBRILLATOR

REDUCING ELECTROCARDIOGRAM ARTIFACTS DURING AND POST CPR

CROSS REFERENCE TO RELATED APPLICATIONS

This patent application claims the benefit of and priority to U.S. Provisional Patent Application Ser. No. 61/926,176, filed on Jan. 10, 2014, titled "System and Method for Reducing ECG Artifact Including During and Post CPR," the disclosure of which is hereby incorporated by references for all purposes. This application is a continuation-in-part of U.S. patent application Ser. No. 13/676,593, entitled "Filter Mechanism for Removing ECG Artifact from Mechanical Chest Compressions," filed Nov. 14, 2012, now U.S. Pat. No. 9,085,545 issued on Jul. 21, 2015; and further this application claims the benefit of U.S. Provisional Application No. 61/616,874 entitled "Visual Rhythm Assessment Meter," filed Mar. 28, 2012; U.S. Provisional Application No. 61/616,727, entitled "ECG Frequency Analysis During CPR," filed Mar. 28, 2012; U.S. Provisional Application No. 61/616,973 entitled "An Analysis during CPR Algorithm Utilizing Shock History," filed Mar. 28, 2012; U.S. Provisional Application 61/616,660 entitled "Guiding Therapy with Real-Time VF Quality Measurement," filed Mar. 28, 2012; U.S. Provisional Application No. 61/616,372 entitled "AED Operation Dependent on Previous Analysis Results," filed Mar. 27, 2012; and U.S. Provisional Application No. 61/616,847 entitled "Method of Integrating Cardiac Rhythm Analysis during CPR into an AED Algorithm" filed Mar. 28, 2012, all of which are hereby incorporated by reference herein in their entirety.

TECHNICAL FIELD

The disclosed subject matter pertains generally to the area of medical devices, and more specifically to the area of external defibrillators and chest compression devices.

BACKGROUND INFORMATION

In normal operation, the heart pumps blood through the various parts of the body in a well-orchestrated fashion. The chambers of the heart contract and expand in periodic harmony, causing the blood to be pumped regularly. In humans, the right atrium sends deoxygenated blood into the right ventricle. The right ventricle pumps blood to the lungs, where the blood becomes oxygenated, and from where it returns to the left atrium. The left atrium pumps the oxygenated blood to the left ventricle. The left ventricle expels the oxygenated blood, forcing it to circulate throughout the body.

The heart chambers pump because of the heart's electrical control system. The sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes the electrical control system of the heart malfunctions, which can cause the heart to beat irregularly, or not at all. The irregular cardiac rhythm is generally called an arrhythmia. Arrhythmias may be caused by electrical activity from locations in the heart other than the SA node. Some types of arrhythmia may result in inadequate blood flow, reducing the amount of blood pumped to the various parts of the body. Some arrhythmias may even result in a Sudden Cardiac Arrest (SCA). In an SCA, the heart fails to pump blood effectively, and, if not treated promptly, death can occur. In fact, it is estimated that SCA results in more than 250,000 deaths per year in the United States alone. SCA may also result from conditions other than an arrhythmia.

One type of arrhythmia associated with SCA is known as Ventricular Fibrillation or "VF." VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, the person will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume properly pumping blood. If VF is not terminated at once, the shock may be repeated, often at escalating energies.

Ventricular Fibrillation can occur unpredictably, even to a person who is not considered at risk and has not been monitored. As such, VF can be experienced by many people who lack the benefit of wearable therapy, such as an Implantable Cardioverter Defibrillator (ICD). If VF occurs to a person, every minute counts. If blood is not flowing to the brain, heart, lungs, and other organs, the person's condition deteriorates rapidly. If resuscitation attempts are to be successful, blood flow must be restored as quickly as possible. Cardiopulmonary Resuscitation (CPR) is one method of forcing blood flow in a person experiencing cardiac arrest. AEDs analyze the patient's electrocardiogram (ECG) to decide whether a patient needs a shock. External defibrillators may also prompt the rescuer to provide chest compressions, rescue breathing, and/or shocks based on established protocols.

In some cases, it is recognized that patients benefit greatly from CPR prior to defibrillation. Properly administered CPR provides oxygenated blood to critical organs of a person in cardiac arrest, thereby minimizing the deterioration that would otherwise occur. For patients with an extended downtime, survival rates are higher if CPR is administered prior to defibrillation. CPR is often critical for a patient's survival from sudden cardiac arrest and is the primary recommended treatment for some patients with some kinds of non-VF cardiac arrest, such as asystole and Pulseless Electrical Activity (PEA). CPR may be a combination of techniques that include chest compressions to force blood circulation, and rescue breathing to force respiration.

In this race against time for human life, being able to, in real-time, understand the optimal amount, durations, pauses, administration frequency of CPR in combination with shock therapy, as well as how to improve and what to do when the CPR quality is poor, is highly desirable. Being able to monitor and analyze, and customize the CPR and the rhythm at the same time and in real-time, determine when to start with a CPR or a shock first, whether to stop altogether, or continue for a longer than routine/protocol-prescribed period to resuscitate successfully, is highly desirable and highly sought after. However, prior attempts, due to issues largely related to noise artifact, have failed to provide an adequate system for successfully monitoring and analyzing rhythms, and other physiological signals and parameters, while performing chest compressions.

Furthermore, the ECG analysis and evaluation at any given point has been held independent of the previous sets of results. Analysis algorithm depends on the signal currently being received from the patient. This signal might be an ECG signal, but it may also include other parameters such as the impedance signal, an accelerometer signal, or the like. Administration of CPR follows a protocol in which the number of compressions, pauses for breaths, and the timing of pauses for analysis have been fixed, and often stand independent of the individual patient's history and needs.

Fixed treatment CPR/shock therapy protocol and rigid analysis algorithms are sub-optimal in many situations. The initial rhythm that is presented when the defibrillator is first connected to the patient is a strong predictor of the course of events for that particular patient. Patients who present with an initial rhythm of VF or ventricular tachycardia (VT) have an approximately 50% chance of being in VF or VT on a subsequent analysis. However, in the subset of patients with a non-shockable initial rhythm and with a no-shock result for every subsequent analysis, there is only an approximate 7% chance that they will be in a shockable rhythm on next analysis. This situation is more extreme for Automated External Defibrillator cases than in Advanced Life Support (ALS) care.

Defibrillator users have a strong desire to analyze an ECG signal accurately to better inform and thereby enhance first-response treatment during the period most critical for cardiac arrest patients. Accordingly, enhancements to the information made available by review of an ECG trace can improve life-saving treatment and enhance the survivability of patients experiencing SCA.

SUMMARY OF EMBODIMENTS

When chest compressions are performed with a mechanical chest compressions device that is operating at a known and precisely controlled frequency, a comb filter will generally do a good job of removing compression artifacts from the ECG signal. However, a comb filter introduces some artifacts of its own, particularly on signals with QRS complexes. Disclosed is a system for reducing undesirable artifacts associated with a filter while retaining the filter's ability to reject compression artifacts.

BRIEF DESCRIPTION OF THE DRAWINGS

FIG. 1 is a diagram of a scene where an external defibrillator is used to try and save the life of a person in accordance with an embodiment.

FIG. 2 is a table listing two main types of the external defibrillator shown in FIG. 1, and who they might be used by.

DETAILED DESCRIPTION

Figure 3:
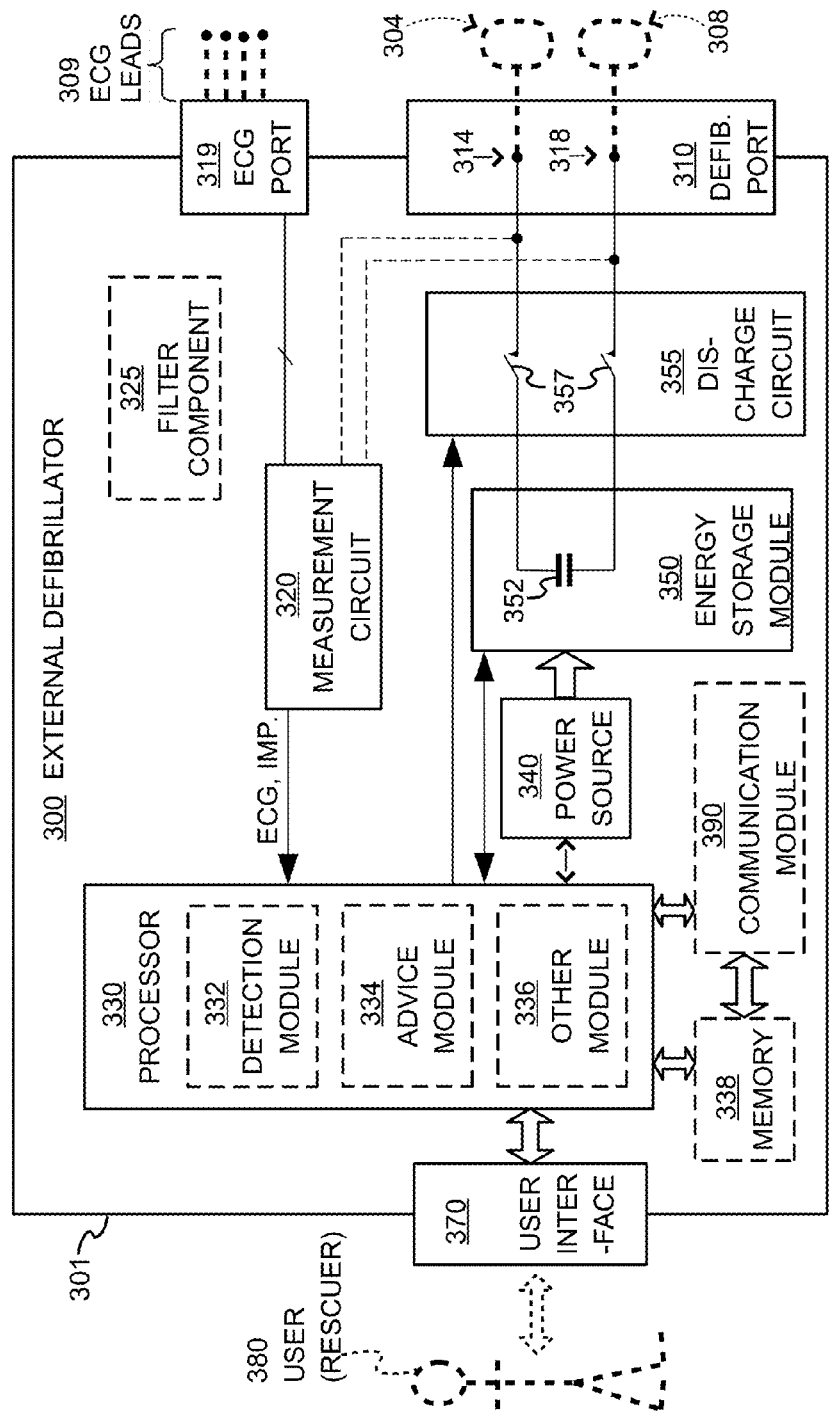
FIG. 3 is a diagram showing components of an external defibrillator 300 made according to embodiments

Generally described, embodiments are directed to improvements in a medical device to provide enhanced ECG information for evaluation by a user of the medical device. In certain embodiments, new artifacts introduced to an ECG trace by filtering out compression artifacts are reduced. In other embodiments, filtering is performed on certain data captured by a medical device to help determine whether a patient has achieved return of spontaneous circulation.

FIG. 1 is a diagram of a defibrillation scene. A person 82 is lying supine. Person 82 could be a patient in a hospital or someone found unconscious. Person 82 is experiencing a condition in their heart 85, which could be, by way of an example, Ventricular Fibrillation (VF).

A portable external defibrillator 100 has been brought close to person 82. The portable external defibrillator can also be a wearable or hybrid defibrillator 82. At least two defibrillation electrodes 104, 108 are usually provided with external defibrillator 100. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing examples of types of external defibrillators and their primary intended users. A first type of defibrillator 100 is generally called a defibrillator-monitor (or monitor-defibrillator) because it is typically formed as a single unit in combination with a patient monitor. A defibrillator-monitor is intended to be used by medical professionals, such as doctors, nurses, paramedics, emergency medical technicians, etc. Such a defibrillator-monitor is generally intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals, such as a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator." An AED typically makes the shock/no shock determination by itself, automatically. It can typically sense enough physiological conditions of the person 82 using only the defibrillation electrodes 104, 108 shown in FIG. 1. An AED can either administer the shock automatically, or instruct the user to do so, e.g. by pushing a button. Being of a much simpler construction, an AED typically costs much less than a defibrillator-monitor. As such, it makes sense for a hospital, for example, to deploy several AEDs throughout, in case the more expensive defibrillator-monitor is engaged at an Intensive Care Unit, or the like.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful when a person suffers from VF because it is so critical to respond quickly. However, the people who will first reach the VF sufferer may not be medical professionals. Increasing awareness has resulted in AEDs being deployed in public or semi-public spaces, so that even a member of the public can use one if they have obtained first aid and CPR/AED training on their own initiative. This way, defibrillation can be administered soon enough after the onset of VF, to hopefully be effective in rescuing the person.

There are other types of external defibrillators in addition to those listed in FIG. 2. For example, a hybrid defibrillator can have aspects of an AED and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1. Plus, the components shown in FIG. 3 can be provided in a housing 301, also known as a casing.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as discussed below.

If defibrillator 300 is a defibrillator-monitor, as was described with reference to FIG. 2, it will typically also have an ECG port 319 in housing 301, for plugging in ECG leads 309. ECG leads 309 can help sense an ECG signal, such as a common 12-lead signal. Other types of ECG signal leads are equally applicable. A defibrillator-monitor could have additional ports that are not shown.

The defibrillator 300 may optionally include a filter component 325 structured to filter the ECG signal. In one specific implementation, the filter component 325 may be a comb filter used to remove chest compression artifacts from the ECG signal. Chest compression artifacts are a type of noise introduced into the ECG signal as a result of chest compressions being delivered to the person 82.

Defibrillator 300 also includes a measurement circuit 320. Measurement circuit 320 receives physiological signals from ECG port 319, and also from other ports, if provided. These physiological signals are sensed, and information about them is rendered by measurement circuit 320 as data, or other signals, etc.

If defibrillator 300 is an AED, it may lack ECG port 319. In that case, measurement circuit 320 could obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330, which may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions to numerous to list here. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, or the like.

Defibrillator 300 moreover includes a discharge circuit 355. Discharge circuit 355 can be controlled to permit the energy stored in module 350 to be discharged to nodes 314, 318, and thus also to defibrillation electrodes 304, 308. Discharge circuit 355 can include one or more switches 357. Those can be made in a number of ways, such as by an H-bridge, or the like.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker to issue audible signals, such as voice prompts, or the like. The user interface 370 may issue prompts to the user 380, visually or audibly, so that the user 380 can administer CPR, for example. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

Figure 4:
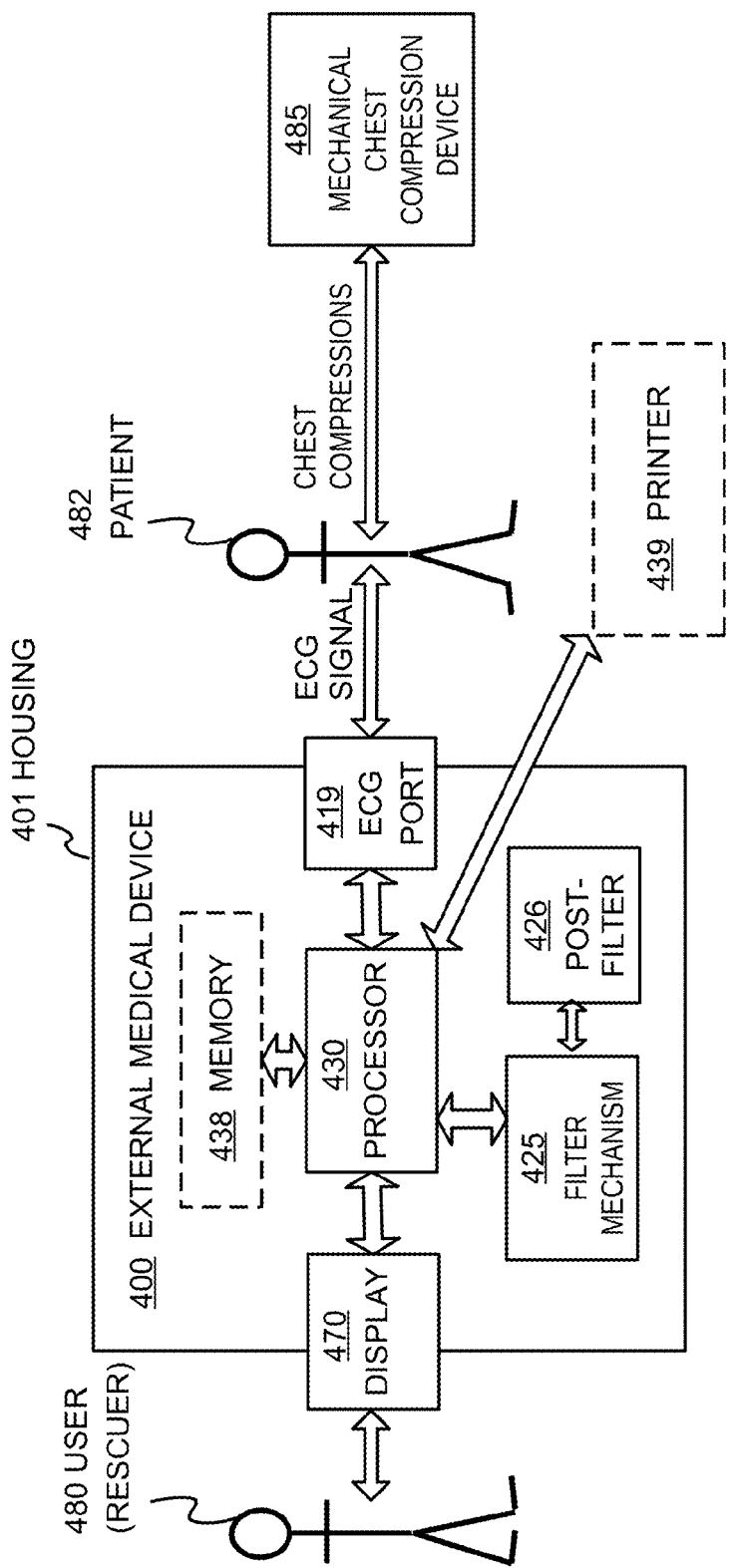
FIG. 4 is a functional block diagram showing components of a patient ECG signal monitoring system according to embodiments.

FIG. 4 is a functional block diagram showing components of a patient ECG signal monitoring system according to embodiments. The system includes an external medical device 400, such as an external defibrillator, having a housing 401, a display 470 in connection with the housing 401, and a processor 430 within the housing 401. One having ordinary skill in the art will recognize that systems according to embodiments generally require no additional sensors or sensor mechanisms than those already provided.

In this example, the system also includes a mechanical chest compression device 485. The mechanical chest compression device 485 may deliver compressions at a highly predictable periodicity, such as 100+/−0.01 compressions/minute, which is 1⅔+/−0.00017 Hz. Such precise frequency control is unusual for typical chest compression devices. An ECG signal may be corrupted by chest compression artifacts corresponding to chest compressions delivered by the chest compression device 485 to the patient 482. Such artifacts may have an artifact fundamental frequency of 1⅔ Hz, and the artifact signal may also contain harmonics of 1⅔ Hz, which will show up at multiples of 1⅔ Hz, i.e., 3⅓ Hz, 5.0 Hz, 6⅔ Hz, etc. The spectral content of these frequency components is generally extremely narrow.

The processor 430 may be configured to receive an input signal containing ECG data for a patient 482 receiving chest compressions from the mechanical chest compression device 485. The input signal may be received via an ECG port 419 in connection with the housing 401. In certain embodiments, the processor 430 is further configured to detect the chest compressions being delivered to the patient 482.

The processor 430 may be further configured to select at least one filter mechanism 425, the mechanical chest compression device 485 having a chest compression frequency f. The mechanical chest compression device 485 may provide an indication of the frequency f to the processor 430.

In certain embodiments, the at least one filter mechanism 425 comprises a comb filter. The comb filter may be non-adaptive. In other embodiments, the at least one filter mechanism 425 comprises a plurality of notch filters. Each of the notch filters may be non-adaptive. In still other embodiments, the at least one filter mechanism 4225 comprises a Weiner filter. One having ordinary skill in the art will readily recognize that various other filter mechanisms may be used in addition to or in place of those mentioned here. Also, multiple filter mechanisms may be used in tandem (either serially or, perhaps, in the alternative).

Certain conventional CPR artifact filters may be adaptive in nature. As used herein, an adaptive filter generally refers to a filter whose transfer function is dependent on the input signal. An adaptive filter may adjust its filter coefficients, center frequency, rolloff, notch width, Q, or other characteristic based on the input signal. Non-adaptive filters according to embodiments generally use predetermined coefficients that may precisely set the transfer function independent of the input signal.

It is possible that embodiments may include multiple non-adaptive filters. The appropriate filter may be selected based on input signal characteristics, such as the frequency content of the ECG signal or impedance signal. Alternatively, the appropriate filter may be selected by communication with the mechanical chest compression device 485, or through a user input selection.

In certain embodiments, the selecting of the at least one filter mechanism 425 is performed responsive to an identification of the mechanical chest compression device 485 being used to deliver the chest compressions to the patient 482. Alternatively or in addition thereto, the processor 430 may be configured to select the at least one filter mechanism 425 responsive to input received from the mechanical chest compression device 485 delivering the chest compressions to the patient 482. In certain embodiments, the processor 430 may be configured to select the at least one filter mechanism 425 responsive to input received from a user 480.

The processor 430 may be configured to apply the at least one filter mechanism 425 to the ECG data to at least substantially remove chest compression artifacts from the ECG data, wherein the chest compression artifacts correspond to the chest compressions being delivered to the patient 482 by the mechanical chest compression device 485, and wherein the at least one filter mechanism 425 substantially rejects content in the frequency f plus content in at least one more frequency that is a higher harmonic to the frequency f. In certain embodiments, application of the at least one filter mechanism 425 to the ECG data reduces an amplitude of the chest compression artifacts by about 20 dB relative to the input signal.

The processor 430 may be further configured to cause the display 470 to visually present the filtered ECG data to the user 480. Alternatively or in addition thereto, the processor 430 may be configured to cause an optional printer 439 to print out the filtered ECG data. In certain embodiments, the processor 430 may cause the filtered ECG to be stored, e.g., by a memory 438, for later review or downloading to a post-event review tool. For the purpose of this discussion, the term "post-event" refers to a time after the occurrence of the SCA episode. Post-event review of the ECG signal may occur, for instance, for training purposes or to assess the therapy that was performed during the event.

In certain embodiments, the processor 430 is preconfigured to apply the at least one filter mechanism 425. In other embodiments, the processor 430 may be configured to apply the at least one filter mechanism 425 to the ECG data responsive to input received from the user 480.

The external medical device 400 further includes a post-filter processing component (post-filter 426). The post-filter 426 is configured to operate either in conjunction with or subsequent to the filter mechanism 425 to enhance data generated by the filter mechanism 425. In one embodiment, the post-filter 426 implements one or more techniques to eliminate filter artifacts introduced to the ECG data by the filter mechanism 425. In other words, the filter mechanism 425 may introduce its own artifacts (e.g., noise) into the ECG data as an unwanted by-product of the filter mechanism 425. The post-filter 426 may include operations to ameliorate or eliminate those unwanted artifacts to further enhance the ECG data.

In certain embodiments, the ECG data is received in real-time. In other embodiments, the ECG data is received in a post-event review. In these embodiments, the ECG data may have been recorded from defibrillation patches or an ECG monitor having multiple leads, e.g., three or more leads. The at least one filter mechanism 425 may be applied to the ECG data regardless of whether the device that recorded the signal even had the at least one filter mechanism 425. Indeed, the ECG data could be provided, e.g., sent via e-mail, to another user who causes the at least one filter mechanism 425 to be applied thereto. Post-event filtering may be used for determining the time of re-fibrillation or examining the signal characteristics prior to fibrillation, for example.

For a patient experiencing VF, VF quality measures such as median VF frequency, Amplitude Spectral Area (AMSA), and a scaling exponent may be used for deciding when to apply chest compressions to the patient 482 and when to defibrillate the patient 482. By applying the at least one filter mechanism 425, these parameters may be accurately measured during CPR.

The processor 430 may be configured to determine a pattern of the chest compression artifacts corresponding to the chest compressions being delivered to the patient 482. The pattern may be based on starting and stopping of the chest compressions being delivered to the patient 482, for example. The processor 430 may be configured to determine whether a chest compression artifact pattern matches an existing chest compression signature. In certain embodiments, the processor 430 may be further configured to merge information corresponding to the pattern with information corresponding to the predetermined pattern responsive to a determination that the pattern matches the existing chest compression signature. In other embodiments, the processor 430 may be configured to generate a new chest compression signature responsive to a determination that the pattern does not match the existing chest compression signature.

In certain embodiments, the processor 430 is configured to suppress application of the at least one filter mechanism 425 to the ECG data responsive to a determination that the mechanical chest compression device 485 is no longer delivering chest compressions to the patient 482. The processor 430 may be further configured to resume application of the at least one filter mechanism 425 to the ECG data responsive to a determination that the mechanical chest compression device 485 has resumed delivery of chest compressions to the patient 482. The presence and/or absence of chest compressions may be detected using a measurement of the impedance signal. For example, the RMS value of a one-second window of the impedance signal is generally a reliable indicator of chest compressions.

In certain embodiments, the processor 430 is configured to generate a report, e.g., CPR statistics, corresponding to the chest compressions that were delivered to the patient 482. Alternatively or in addition thereto, the processor 430 may be configured to generate a report corresponding to the mechanical chest compression device 485 that was used to deliver the chest compressions to the patient 482.

In certain embodiments, the processor 430 is further configured to monitor an impedance signal corresponding to the patient. An impedance waveform could be filtered to remove compression artifacts, for example, to allow for detection of ventilation artifacts or the presence of cardiac output. The processor 430 may be further configured to detect return of spontaneous circulation (ROSC) by applying a signal-averaging filter to the impedance signal, e.g., combining a comb filter with the signal-averaging filter.

In certain embodiments, the processor 430 is further configured to analyze the filtered ECG data. In these embodiments, the processor 430 may be further configured to make a shock/no shock decision based on the analysis of the filtered ECG data.

In certain embodiments, the chest compressions are manually delivered to the patient 482 by the rescuer 480. In these embodiments, the rescuer 480 may use a metronome while delivering the chest compressions to the patient 482 in order to deliver compressions at a very precise rate, for example. The processor 430 may be configured to select the at least one filter mechanism 425 based at least in part on a chest compression rate corresponding to the chest compressions being delivered to the patient 482. These embodiments may further include informing the rescuer 480 whether the CPR is currently effective, i.e., the chest compressions are being administered at the correct rate. The rescuer 480 may thus judge whether to trust the filtered display 470.

In certain embodiments, the device 400 further includes an energy storage module within the housing 401 for storing an electrical charge and a defibrillation port for guiding via electrodes the stored electrical charge to the patient 482.

Enhanced Detection of Return of Spontaneous Circulation (ROSC)

Rescuers need to know when a cardiac arrest patient has ROSC (Return of Spontaneous Circulation) in order to determine when to stop chest compressions. Chest compressions on top of ROSC may be harmful because it may be pro-arrhythmic and it may hinder cardiac output. Currently rescuers have no way of determining whether a patient has ROSC during chest compressions because it is difficult to separate blood flow that is generated by chest compressions from blood flow generated by the heart.

A pulse cannot be easily palpated during chest compressions because the compressions themselves produce blood flow that can be felt. Sometimes rescuers use End-Tidal CO2 (EtCO2) readings as an indication of whether the patient may have a pulse, but they always verify ROSC by manual palpation during a pause in chest compressions. However, manual palpation is known to be inaccurate and can lead to inappropriate compressions for a patient experiencing ROSC. At the same time, chest compression pauses are known to be detrimental to survival.

One technique of automatically detecting the presence of a pulse was proposed in U.S. Pat. No. 8,092,392 (Pulse Detection Method and Apparatus using Patient Impedance). That technique of detecting a pulse involves capturing an ECG signal and an impedance signal; detecting QRS complexes in the ECG signal; selecting corresponding segments of the impedance signal; and looking for features of the impedance signal that specifically correspond with the QRS complexes.

The term "QRS complex" refers to the combination of three graphical deflections seen on a typical electrocardiogram (ECG) trace. For a normally functioning heart, the QRS complex is usually the central and most visually obvious part of the trace. It corresponds to the depolarization of the right and left ventricles of the human heart.

Figure 5:
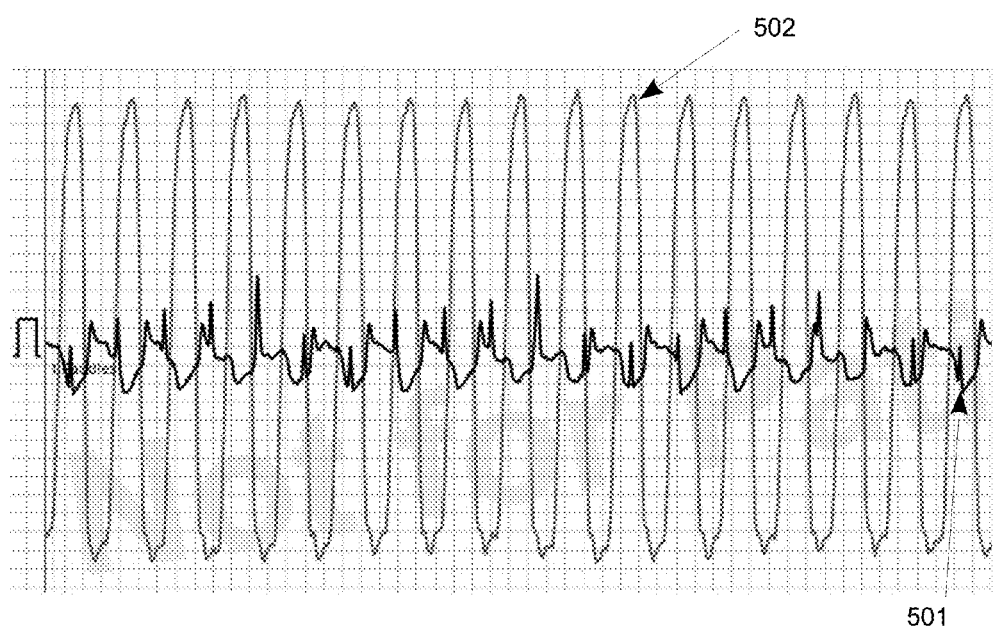
FIG. 5 is shows an ECG signal and impedance signal from a cardiac arrest patient receiving chest compressions.

The technique described in U.S. Pat. No. 8,092,392 may work during a pause in chest compressions, but when compressions are ongoing, that technique does not separate the portion of the impedance signal related to cardiac blood flow from the impedance signal inherent in chest compressions. For example, FIG. 5 shows an ECG signal (1001) and impedance signal (1002) from a cardiac arrest patient receiving chest compressions. The ECG signal contains compression artifacts approximately the same amplitude as the QRS complexes, making automatic QRS detection difficult. The impedance signal clearly shows chest compressions. Any evidence of a pulse that may be present on the impedance signal is overwhelmed by the chest compressions.

Figure 6:
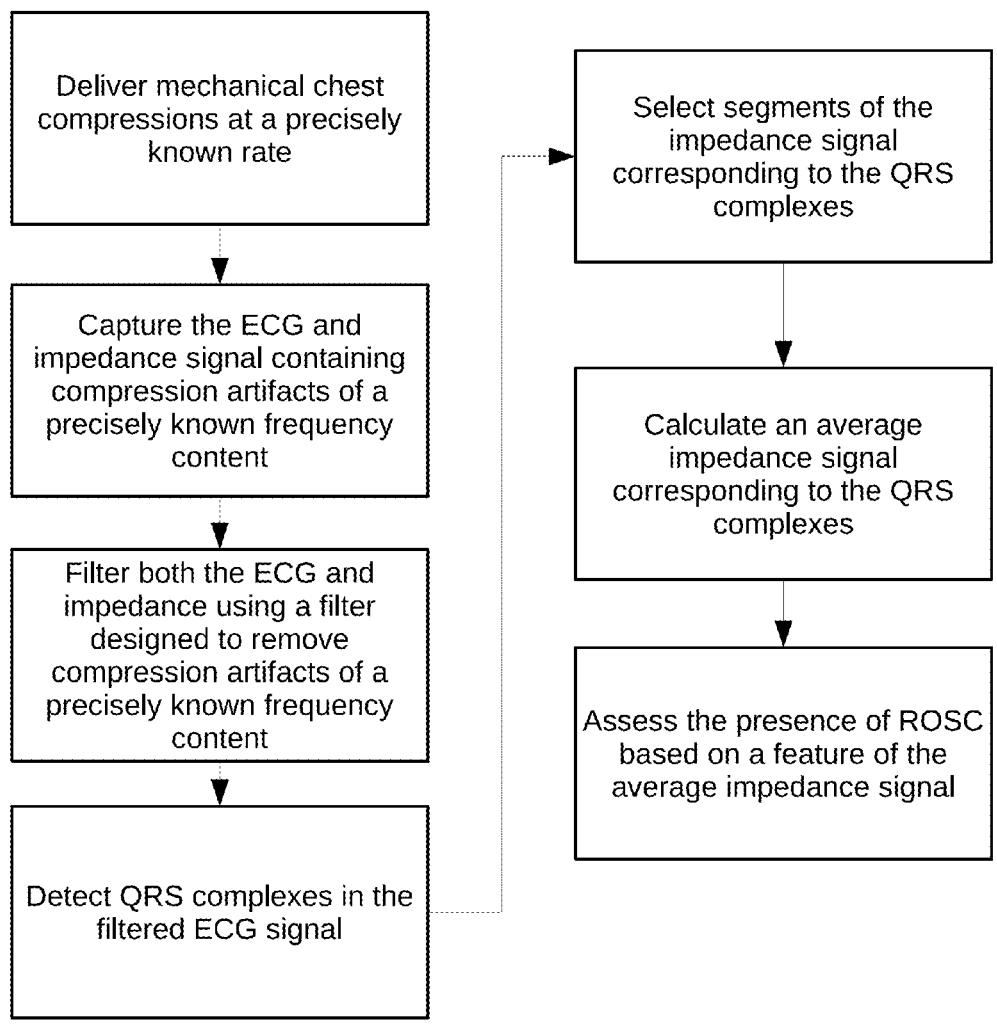
FIG. 6 is a flow diagram generally illustrating one illustrative method of detecting a pulse while mechanical chest compressions are ongoing.

FIG. 6 is a flow diagram generally illustrating one illustrative method of detecting a pulse while mechanical chest compressions are ongoing. The method involves generally performing the steps that follow.

First, mechanical chest compressions are being delivered at a precisely known rate. (Step 601). Because the compressions are delivered at a known rate, they produce predictable artifacts.

Second, the ECG and impedance signals of the patient are captured. (Step 602). Those signals contain compression artifacts of a precisely known frequency content because they are delivered at a consistent and known rate.

Third, both the ECG and impedance signals are filtered using a filter designed to remove compression artifacts of a precisely known frequency content. (Step 603). In one embodiment, a comb filter is used. In other embodiments, other filters that operate on predictable signals can be used.

Fourth, the QRS complexes in the filtered ECG signal are detected. (Step 604). Any appropriate technique may be used to detect the QRS complexes. Many techniques are known for detecting QRS complexes in an ECG signal.

Fifth, segments of the impedance signal corresponding to the QRS complexes are selected. (Step 605). In other words, an attempt is made to isolate a periodicity within the impedance signal that corresponds to the periodicity of the QRS complexes. When done, the impedance signal is segmented such that essentially each cycle of the impedance signal is overlaid with a corresponding cycle of the QRS complexes.

Sixth, an average impedance signal is calculated. (Step 606). The average impedance signal corresponds to the QRS complexes.

Seventh, the presence of ROSC is assessed based on a feature of the average impedance signal. (Step 607).

Figure 7:
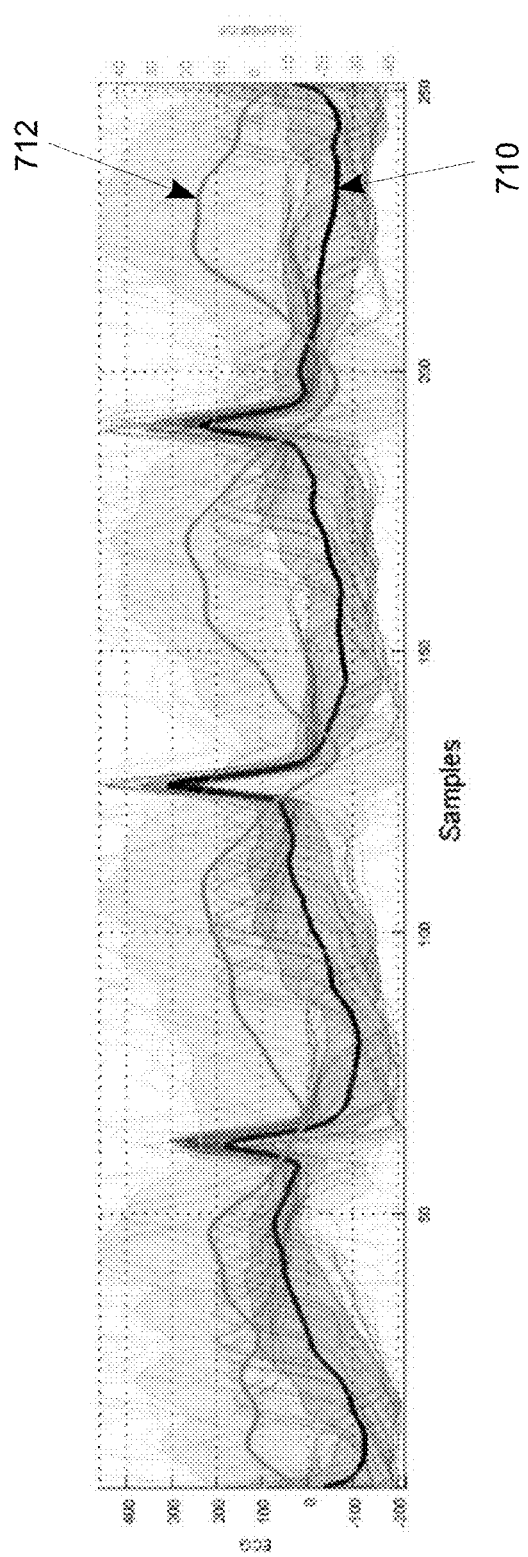
FIG. 7 illustrates the technique described in connection with FIG. 6.

FIG. 7 illustrates the technique just described. The trace was taken from a cardiac arrest patient who was being treated with mechanical chest compressions using a mechanical chest compression device (e.g., a Lucas 2 device) at a 1.666 Hz rate. To generate the trace shown in FIG. 7, ECG and impedance signals were collected during chest compressions. QRS complexes were detected on the ECG (black) signal. Successive complexes were overlaid with the peaks aligned at about sample number 125. The average ECG signal is shown in dark black 710. The impedance (blue) signal was filtered with a comb filter designed to removed 1.666 Hz and all of its harmonics. Segments of the impedance signal that correspond with each QRS complex were overlaid and time-averaged to create the dark blue signal 712.

The traces in FIG. 7 show that the impedance signal contains an oscillation with one cycle for each QRS complex. The fact that the impedance oscillation is synchronous with QRS complexes indicates that it is likely caused by cardiac-generated blood flow (i.e. ROSC, or a pulse). If the activity on the impedance channel had not been cardiac-generated, then it would probably not line up with the QRS complexes as well.

Figure 8:
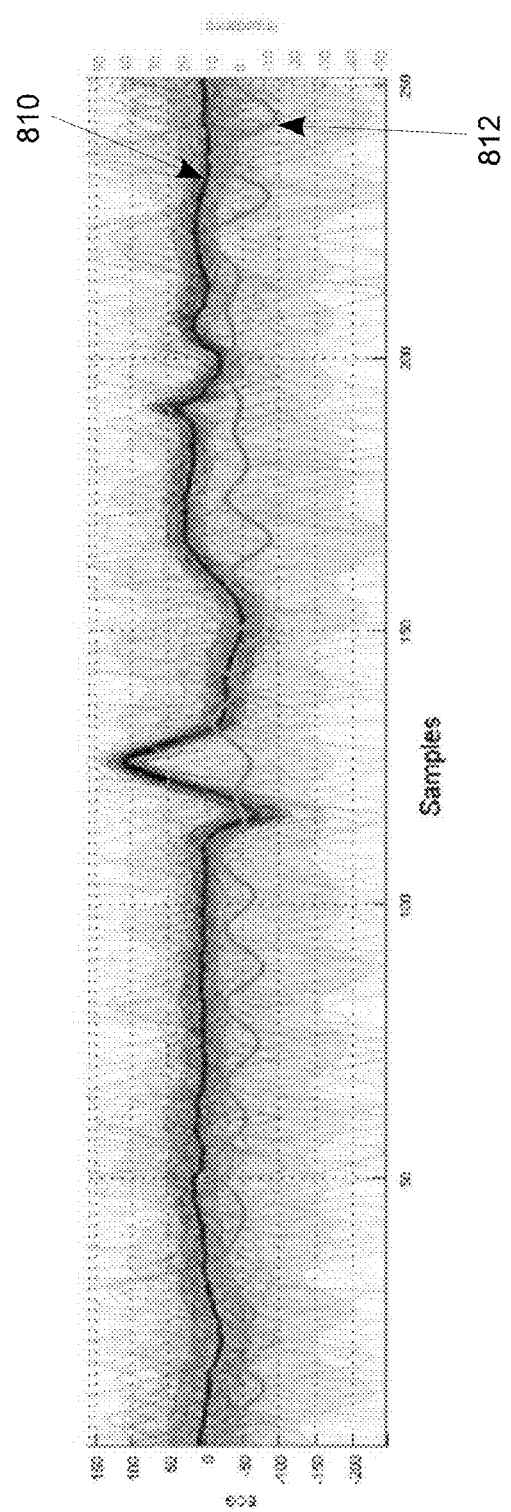
FIG. 8 illustrates what the impedance and ECG signals look like if the patient has no pulse

FIG. 8 illustrates what the impedance and ECG signals look like if the patient has no pulse. In FIG. 8 the average impedance signal 812 is not time-aligned with the average QRS complex signal 810, so it is unlikely that any activity seen on the impedance channel is related to cardiac-generated blood flow. Accordingly, it is unlikely that the patient is experiencing ROSC.

This technique for detecting a pulse could be used to automatically stop the chest compressions when the patient has a pulse. In one embodiment, a chest compression device that has the ability to monitor ECG and impedance could verify that the patient does not have a pulse before starting chest compressions, and could also automatically stop chest compressions when a pulse returns. In another embodiment, a system in which the chest compression device is separate from the ECG/impedance monitor but that includes communication between the two could also operate in this manner. Such a fully automatic approach has the advantage of being very easy to use, allowing EMTs and possibly lay rescuers to use a mechanical chest compression device with reduced fear of harming the patient.

In yet another embodiment, this technique for detecting a pulse could also be used in an advisory manner. In this embodiment the ECG/impedance monitor could inform the operator of whether the patient has a pulse and the operator would then decide whether to provide mechanical chest compressions or not. An advisory approach has the advantage of not requiring communication between the chest compression device and the monitor, but still being very easy for the rescuer to use.

It is also possible that this technique for detecting a pulse could be applied in a "manual mode" that allows the rescuer to look at the signals and decide whether it is likely that the patient has a pulse. In this embodiment a display would be provided that overlays a set of QRS complexes and the associated segments of the impedance waveform in a manner that is similar to one of the figures in this disclosure. The rescuer could then decide whether the patient has a pulse and whether chest compressions should be applied. This embodiment may allow the rescuers to distinguish between a strong and a weak pulse and to exercise some judgment about how to treat each particular patient.

These embodiments have focused on using the impedance signal in conjunction with the ECG to detect a pulse, but it is possible that other signals may be used in a similar manner. In fact, any signal that is indicative of blood flow could be used instead of the impedance signal to produce a similar effect. For example, the plethysmograph signal from a pulse oximeter could be used instead of the impedance to detect a cardiac-generated pulse during compressions. Similarly, the signal from the pressure sensor of a partially inflated blood pressure cuff could be used. It is possible that heart sounds could be used.

Enhanced ECG Filtering for Post-Event Review

One embodiment of the foregoing technique employs a filter mechanism 425, such as a comb filter, to ameliorate compression artifacts introduced by a mechanical chest compression device to an impedance signal. The resultant signal improves detectability of ROSC while mechanical chest compressions are ongoing. Digital filters are also used to remove compression artifacts from QRS complexes in an ECG trace. However, one characteristic of some filters (such as a comb filter) is that they take time to learn the input signal before they can produce a properly filtered output.

Figure 9:
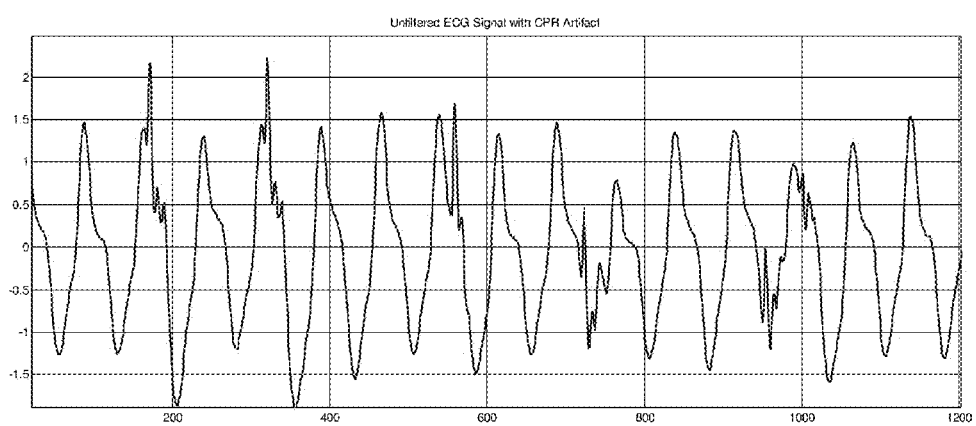
FIG. 9 is an ECG signal acquired from a pulseless patient receiving CPR with a mechanical chest compression device.

For example, FIG. 9 is an ECG signal 900 acquired from a pulseless patient receiving CPR with a mechanical chest compression device. As can be seen from FIG. 9, compression artifacts 901 are present as a result of a mechanical compression device.

Figure 10:
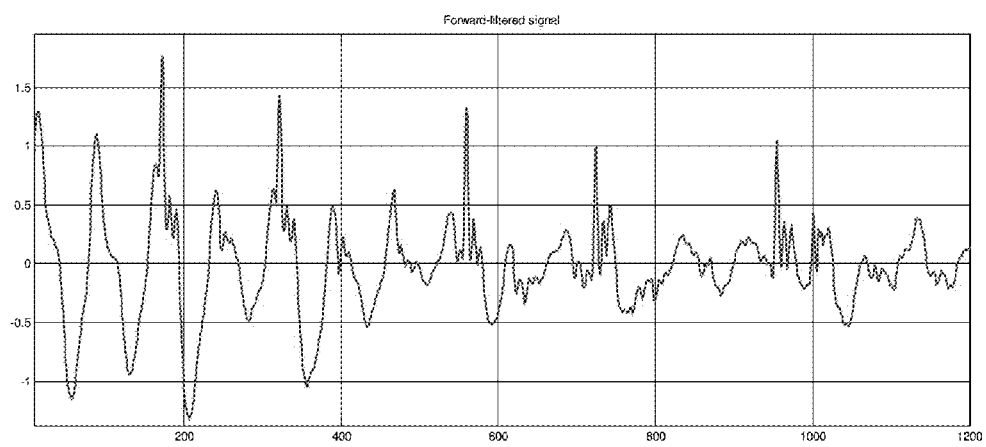
FIG. 10 is the signal shown in FIG. 9 after it has been filtered with filter mechanism.

FIG. 10 is the same signal after it has been filtered with filter mechanism 425, such as a comb filter. The filter removes a large portion of the artifact 901, presenting a signal that is intelligible by medical personnel. However, the filtered version has some limitations. One of the limitations is that, in this embodiment, the filter mechanism 425 requires 8 to 10 compressions to "learn" the artifact 901 and begin effective filtering. This learning curve is undesirable because the signal continues to be corrupted by compression artifacts during that period.

During a live SCA event, the ECG signal must be monitored in real time. However, during post-event review, the system already has the benefit of stored ECG data captured during the SCA event. Thus, the inventor has developed a technique to avoid the typical learning curve associated with a common filter, such as a comb filter.

Figure 11:
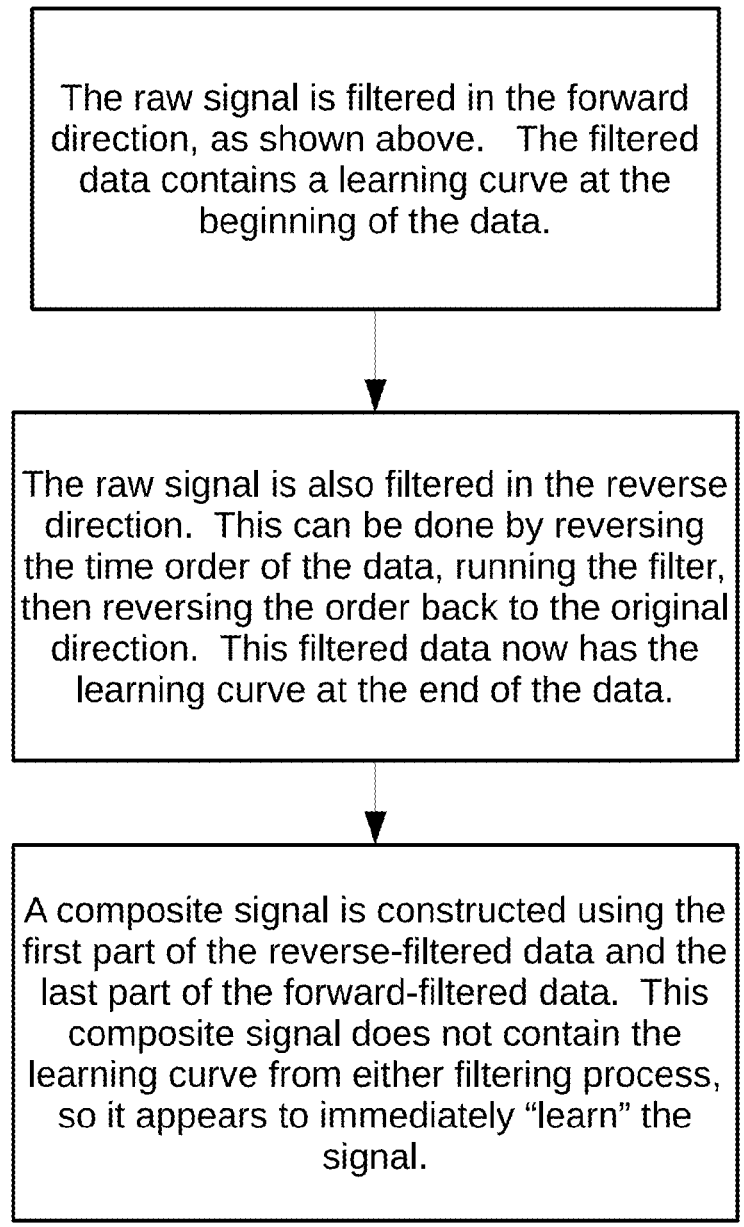
FIG. 11 is flow diagram generally illustrating a method for ameliorating a learning curve from filtered ECG captured during an SCA event.

FIG. 11 is flow diagram generally illustrating a method for ameliorating a learning curve from filtered ECG captured during an SCA event. Alternatively, the method could operate on ECG trace data that was captured during an SCA event and which demonstrates the effect of a learning curve associated with a filter mechanism used to ameliorate compression artifacts.

First, the raw ECG signal is filtered in the forward direction. (Step 1101). An example of such forward filtering is shown in FIG. 10. The filtered data contains a learning curve at the beginning of the data.

Second, the raw signal is also filtered in the reverse direction. (Step 1102). This can be done by reversing the time order of the ECG data, running the filter, then reversing the order back to the original direction. This filtered data now has the learning curve at the end of the data.

Third, a composite signal is constructed using the early part of the reverse-filtered data and the latter part of the forward-filtered data. (Step 1103). In other words, the learning curve portion of each of the filtered sets of data is eliminated, and the post-learning curve portions of each of the filtered sets of data are joined to form one set of filtered data that does not exhibit the learning curve artifacts. The composite signal does not contain the learning curve from either filtering process, so it appears to immediately "learn" the signal.

Figure 12:
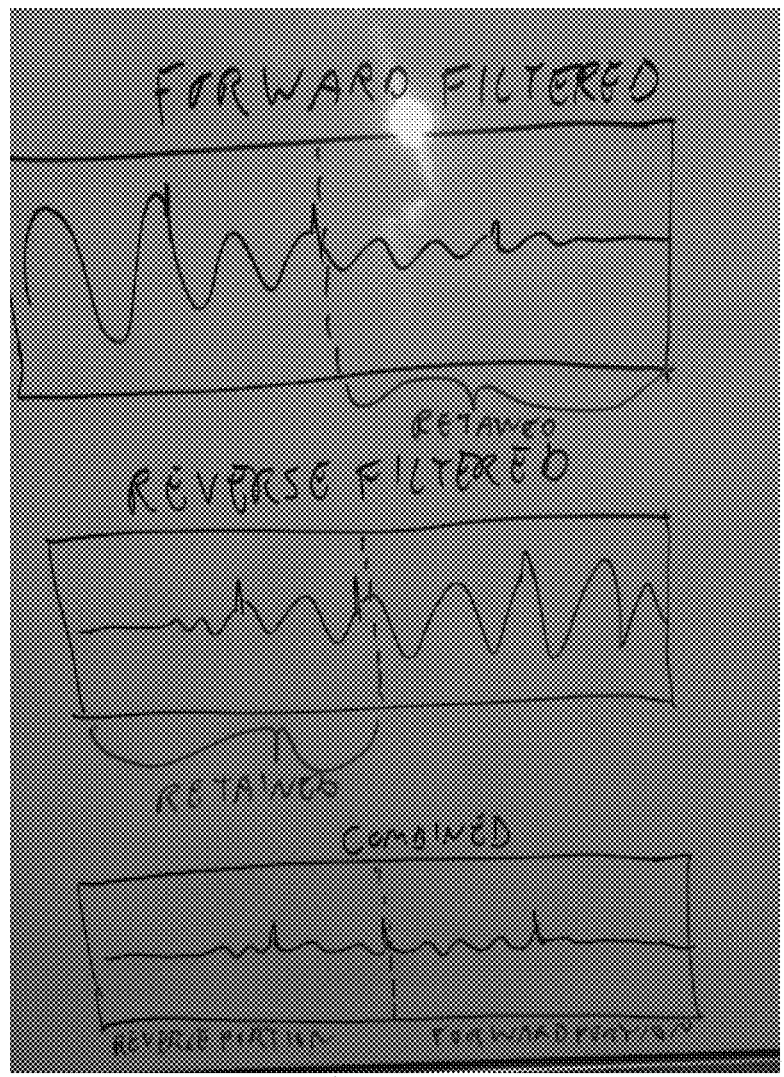
FIG. 12 is a series of waveforms generally illustrating the process described in connection with FIG. 11.

The process is generally illustrated in FIG. 12. A filter mechanism, such as a comb filter, can be used in real-time (e.g. to display a filtered signal on the LP15) or it can be used in post-event review (e.g. as part of Code-Stat, available from Physio-Control, Inc.). In a real-time application, reverse filtering is not possible because it would require the device to predict the future. However, in post-event review it is possible to filter in both directions.

In actual use, the filter learning curve may not simply occur once, it may happen many times, such as each time the filter is started and stopped. The figure below is an illustration of the CPR performed during a cardiac arrest case. The red bars represent chest compressions.

Figure 13:
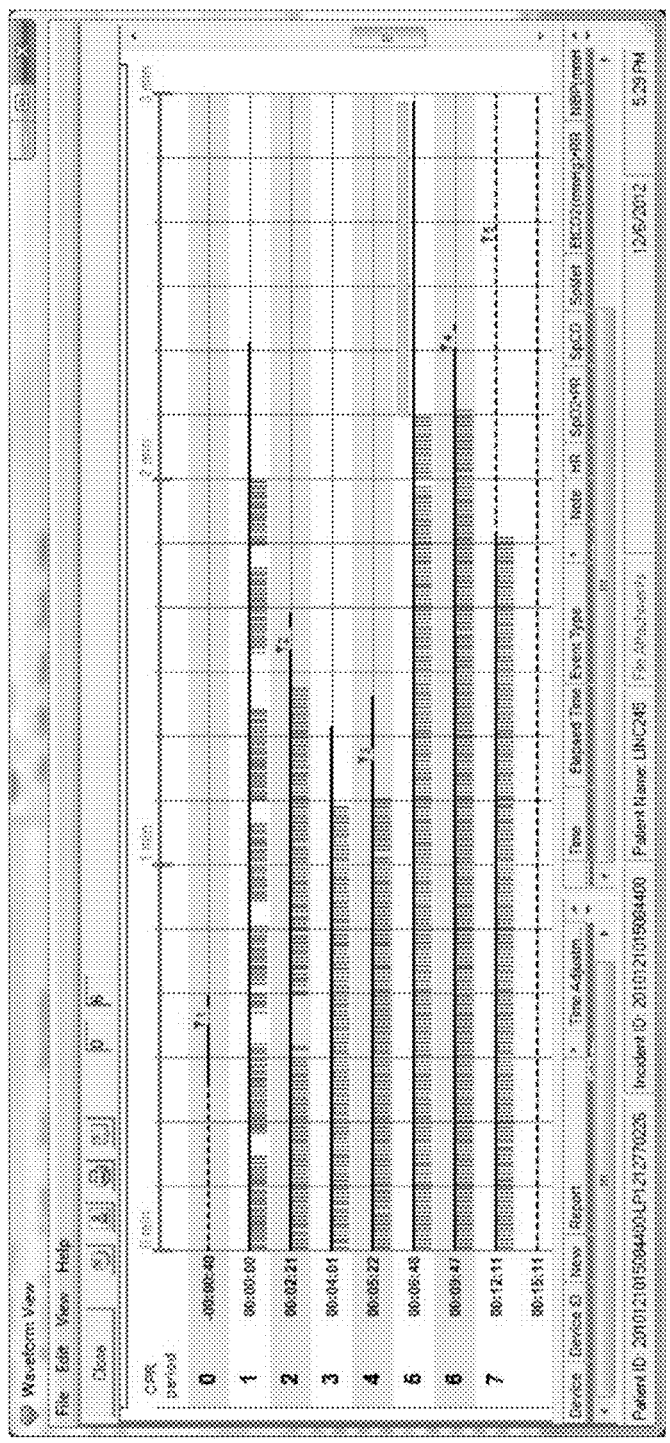
FIG. 13 is a waveform view that shows how often compressions are started and stopped.

FIG. 13 is a waveform view that shows how often compressions are started and stopped. Typically, a filter mechanism has a learning curve that can be observed when compressions are either started or stopped. When compressions are stopped the filter, in effect, needs to un-learn the artifact. This causes the filter to insert artifact into a signal that would otherwise be clean.

When compressions are stopped it is possible to avoid displaying artifact by simply detecting that chest compressions have stopped and switching the display from the filtered signal to the unfiltered signal. When compressions are resumed the display would begin displaying the filtered signal again.

Figure 14:
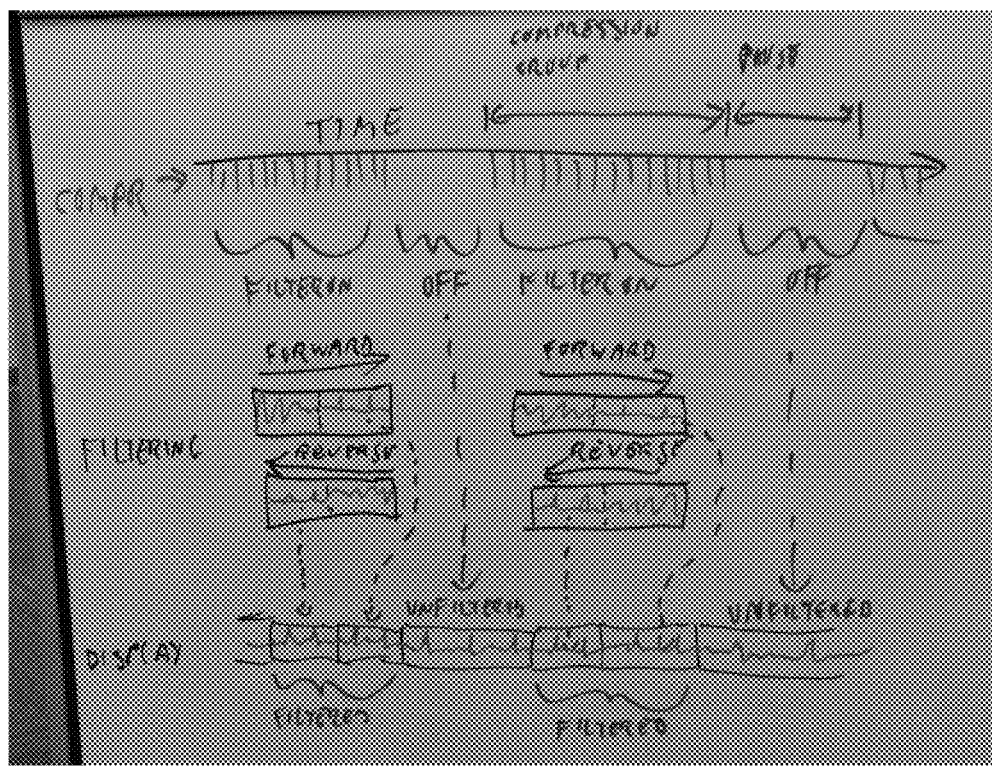
FIG. 14 illustrates a sequence of using filtered and unfiltered data.

FIG. 14 illustrates the sequence of using the filtered and unfiltered data. Each compression group is processed together using the selective forward-reverse filtering process. Unfiltered data is used during compression pauses.

In the preferred embodiment, the process of switching between the filtered and unfiltered data can be used in a real-time display, but the selective forward-reverse filtering can only be used for post-event review.

In implementations of the process, chest compressions should be identified. This can be done using a compression detection algorithm such as that available in Code-Stat available from Physio-Control, Inc. That compression detector uses the impedance signal recorded by the defibrillator to locate chest compressions. Alternatively, the compressions could be identified via communication with the chest compression device. This communication could be real-time (e.g. with a wireless link) or it could be through a post-event data download. If the defibrillator downloads the ECG signal and the chest compression device downloads compression information, the compression information could be used to help filter the ECG signal.

Post-Filter Processing of ECG Trace

When chest compressions are performed with a mechanical chest compressions device (such as Lucas) that is operating at a known and precisely controlled frequency, a filter mechanism, such as a comb filter, will generally do a good job of removing compression artifacts from the ECG signal. However, a comb filter introduces some artifacts of its own, particularly on signals with QRS complexes. The inventor has developed a technique for reducing undesirable artifacts associated with a filter mechanism while retaining the filter mechanism's ability to reject compression artifacts.

Figure 15:
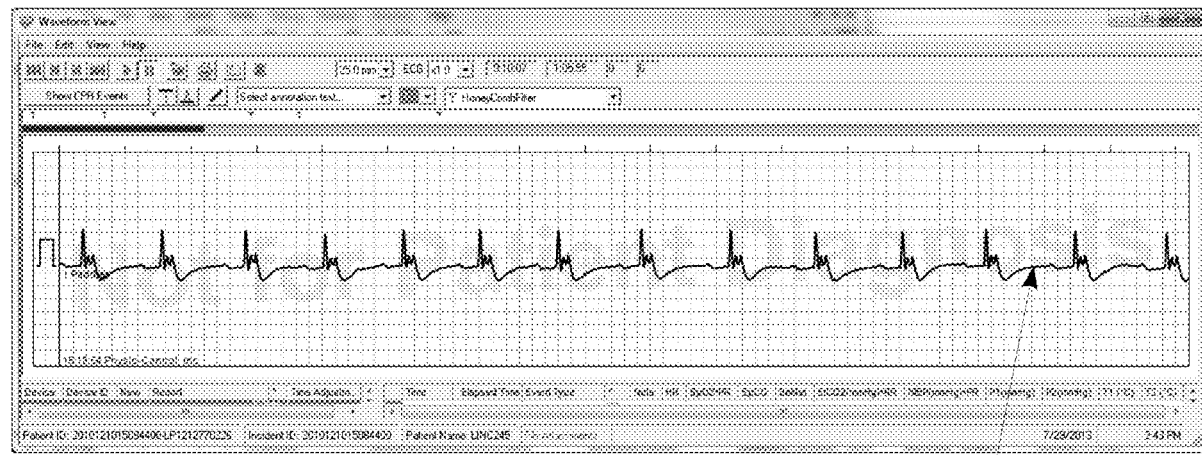
FIG. 15 is an example of an unfiltered signal with QRS complexes.
Figure 16:
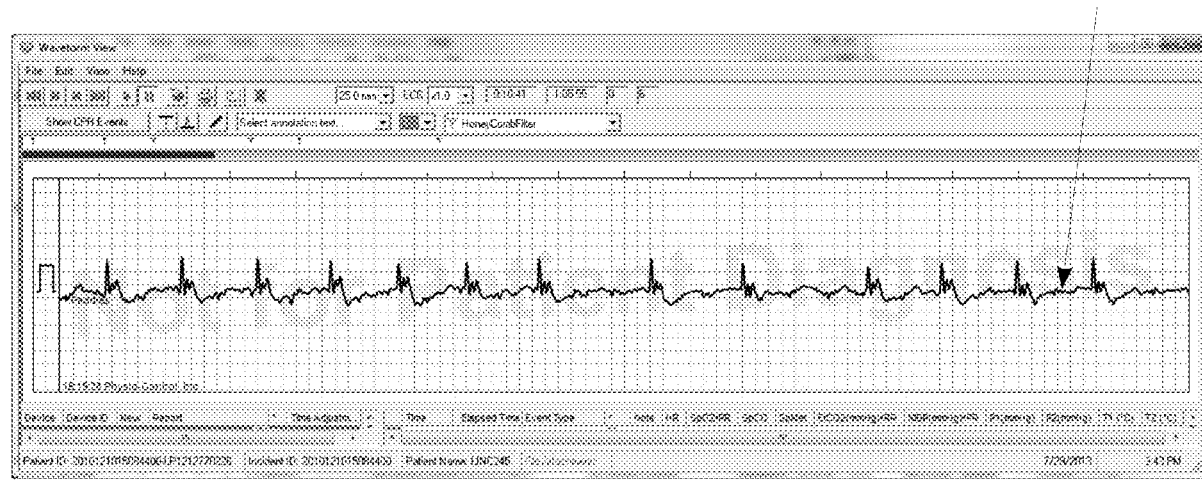
FIG. 16 is an example of the ECG signal shown in FIG. 15 after having been filtered.

For example, a comb filter has an unusual impulse response, which causes the filter to add some baseline distortion to a signal with QRS complexes. This impulse response is not a problem for VF or asystole, but can cause noticeable baseline distortion when QRS complexes are present. FIG. 15 is an example of an unfiltered signal with QRS complexes. Note that the baseline 1503 is free of any compression artifacts. FIG. 16 is an example of the ECG signal shown in FIG. 15 after having been filtered, such as using a comb filter. Note that the filtered signal shown in FIG. 16 has additional noise 1603 on the baseline that is not present in the unfiltered signal (5103). Although this baseline noise is unlikely to affect a shock/no-shock decision, it does represent a distortion that is undesirable.

The inventor has developed several methods for reducing the baseline noise associated with a comb filter removing compression artifacts.

First Method

One embodiment of a method for reducing baseline noise is to detect peaks in the signal that are unusually tall, calculate the impulse response that each peak could cause, then subtract the calculated impulse response from the filtered signal.

Figure 17:
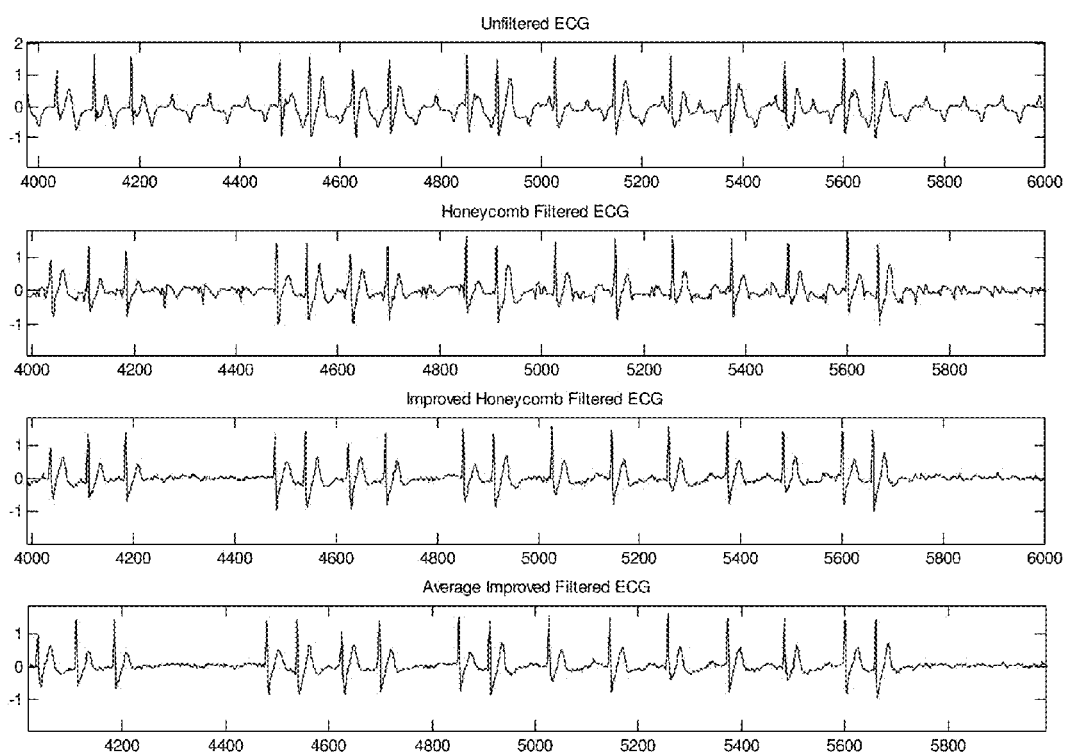
FIG. 17 is a series of traces which generally illustrate the operation of embodiments according to one implementation.

In FIG. 17, the top trace shows the unfiltered ECG signal with mechanical compression artifact. The signal contains QRS complexes that are approximately twice as tall as the artifact. the compression artifact is particularly evident between data points 4200 and 4400, and between 5800 and 6000.

The middle trace in this figure shows the comb-filtered signal, which has less compression artifact, but has a different sort of artifact that is caused by an interaction of the QRS complexes with the impulse response of the filter. This artifact is particularly noticeable between data points 4200 and 4400.

The bottom trace shows the output from an improved comb filter. The impulse response-related artifacts are much smaller. To derive this signal, the input was first filtered with a standard comb filter. Next, outlier data points were found on the comb-filtered signal by finding all points that exceed two times the median of the absolute value of the signal over a 1 second window. In this example, the first 8 impulse response artifacts were subtracted for each of these outlier data points.

This implementation overcomes one of the biggest limitations of a comb filter—baseline artifacts caused by the filter itself. These artifacts are not a problem for patients in VF or asystole, but they can be annoying when QRS complexes are present. By significantly reducing the artifacts associated with QRS peaks this invention represents a substantial improvement over a conventional comb filter.

This invention proposes the selective removal of impulse response artifacts related to signal peaks. It is important to note that this technique would not work if it were not selective. While it is technically possible to un-do the impulse response effects on the entire signal, such an approach would not be beneficial because comb filter impulse response is necessary for removal of compression artifacts. To un-do the impulse response would be the same as un-doing the artifact filtering. This invention is able to remove the impulse response artifacts for a limited number of data points, reducing the undesirable impulse response artifacts while retaining the compression artifact filtering that is desired.

This invention is distinct from previously-known adaptive filters. Adaptive filters modify the filter coefficients based on historical data. An adaptive filter essentially "learns" the signal characteristics and optimizes itself accordingly. Whatever the coefficients are at any given point in time, all of the incoming data is filtered by those same coefficients.

This invention is distinct from adaptive filters because there is not learning involved. All data points are processed with the same comb filter. The effect of the impulse response is then removed from the filtered signal for a few selective data points.

Second Method

In another embodiment, an average forward and reverse filtering is employed. This implementation takes advantage of filters which can be non-causal. For example, the Code-Stat software does so by running a comb filter in both directions. It then displays the forward filtered signal for the second half of the segment and it displays the second half of the reverse filtered signal for the first half of the segment. This technique avoids start up transients at either end of a CPR segment.

The idea for reducing artifacts is to average the forward and reverse filtered signals. The artifacts fall on opposite sides of the QRS complexes, depending on the direction of the filtering, so by averaging the two together the amplitude should be cut in half.

Figure 18:
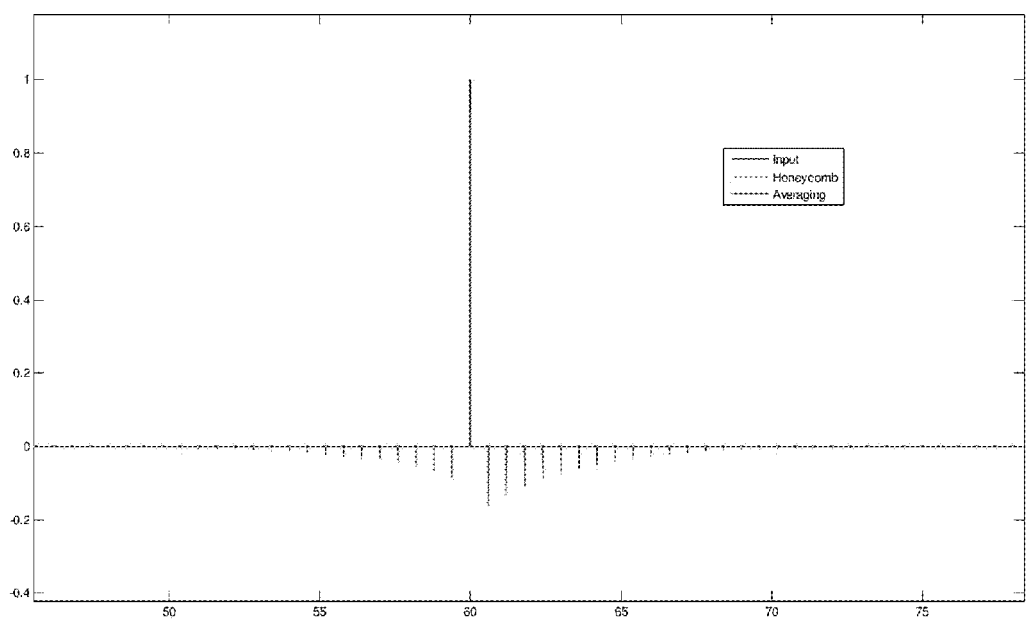
FIG. 18 is an illustration of the benefits of embodiments that implement forward-reverse averaging.

FIG. 18 is an illustration of the benefits of embodiments that implement forward-reverse averaging. The input is a single impulse of amplitude 1 (blue). The conventional comb filter (green) has negative going artifacts that are all to the right of the impulse. The signal with forward-reverse averaging (red) has artifacts on both sides of the impulse, but they are of a reduced amplitude compared to the conventional comb filter.

Figure 19:
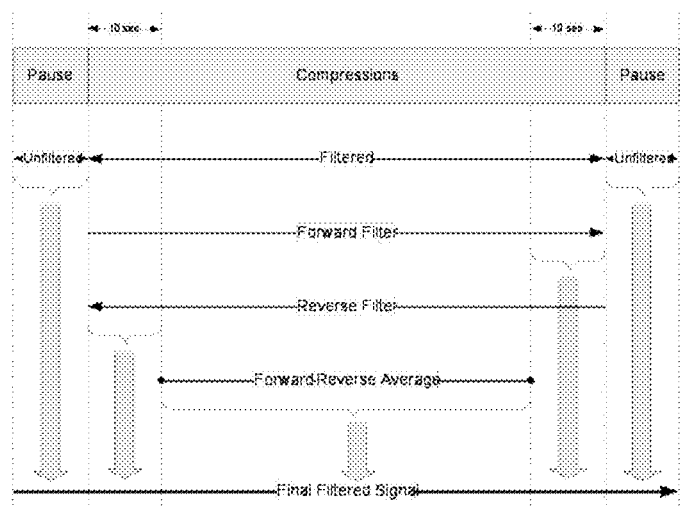
FIG. 19 represents an illustration of an implementation of forward-reverse averaging in accordance with one embodiment.
Figure 20:
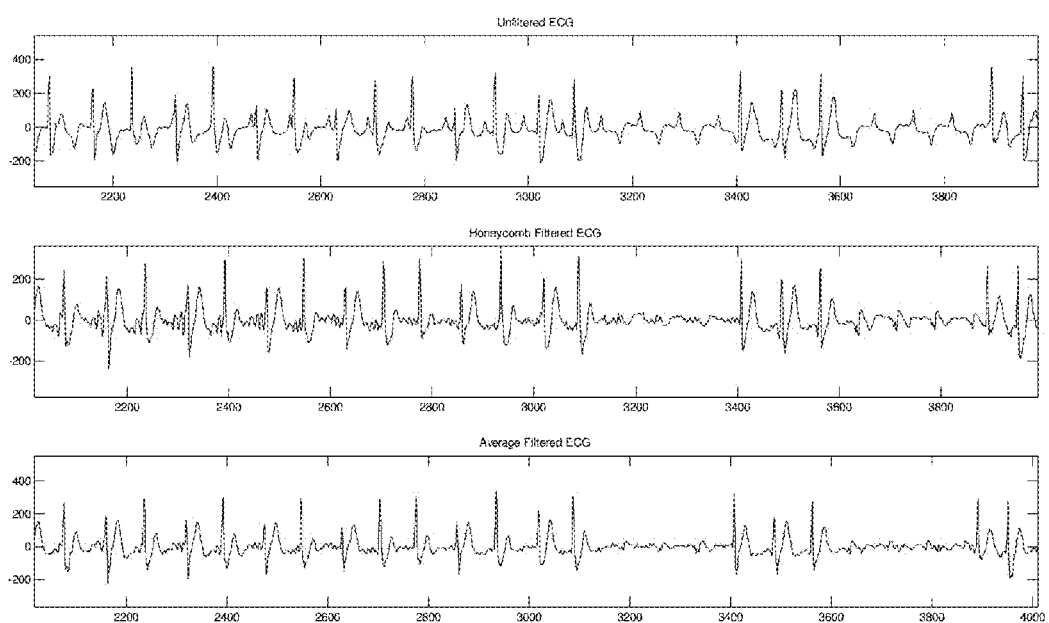
FIGS. 20 to 23 illustrate examples of various traces implementing one particular embodiment.

If the forward-reverse averaging was implemented in an embodiment, it is important that it be applied in the proper manner. FIG. 19 represents an illustration of such an implementation. The averaged signal cuts the amplitude of the impulse artifacts in half, but there are now twice as many of them. FIG. 20 is a portion of LINC059_18 that shows the difference.

There is a benefit to averaging, but the benefit may be limited. Averaging such as this can be done in post-review applications, but cannot be done in real-time display applications because unless such applications had access to future data somehow (e.g., perhaps based on some manner of prediction).

Third Method

In yet another embodiment, a method may be implemented to perform a filtering process in both a forward and reverse direction. As discussed above, in embodiments which use a filter that generates artifacts at predictable periods, such as a comb filter. In such an embodiment, the artifact may be a negative value having an amplitude which decreases with time. Because the artifacts occur only after the signal (e.g., a QRS complex) that generates the artifact, the forward and reverse signals will have negative artifacts which follow the original signal in the forward direction, but which precede the signal (in time) in the reverse direction.

Thus, by overlaying both the forward and reverse processed signals, an embodiment may reject the signal having the larger absolute value. The result of such a technique is the original signal (e.g., the QRS complex) will have nearly the same absolute value in both directions, but the artifacts would only have significant values in opposing directions. In other words, the artifacts would have no value (or nearly no value) on the left of the chart (as illustrated in FIG. 18) for forward-filtering, while the artifacts would have no value (or nearly no value) to the right of the chart for reverse-filtering. Thus, the absolute values of the combination of the two directions would, in essence, cancel those artifacts.

Set out below is illustrative Matlab code to implement the core concepts of this particular embodiment:

```
%Select for signal with minimum absolute value
for i=1:length(forwardECG)
    if (abs(forwardECG(i))<abs(reversECG(i)) &&
    abs(forwardECG(i))<abs(avgECG(i)))
        Mecg(i)=forwardECG(i);
    elseif abs(reversECG(i))<abs(avgECG(i))
        Mecg(i)=reversECG(i);
    else Mecg(i)=avgECG(i);
    end
end
```

Fourth Method

In still another embodiment, a method may be implemented which incorporates elements of both averaging and absolute-value processing. Set out below is illustrative Matlab code to implement the core concepts of one particular embodiment:

```
%select for signal with data continuity
Secg(1)=avgECG(1);
for i=2:length(forwardECG)
    if abs(forwardECG(i)) - abs(reversECG(i)) <0.5*abs(avgECG(i)) || 
    ...
            abs(forwardECG(i)) - abs(reversECG(i))<.05
        Secg(i)=avgECG(i);
    elseif abs(forwardECG(i) - (Secg(i-1)))< abs(reversECG(i) -
    (Secg(i-1)))
&& ...
            abs(forwardECG(i) - (Secg(i-1)))< abs(avgECG(i) -
            (Secg(i-1)))
        Secg(i)=forwardECG(i);
    elseif abs(reversECG(i) - (Secg(i-1)))< abs(avgECG(i) -
    (Secg(i-1)))
        Secg(i)=reversECG(i);
    else Secg(i)=avgECG(i);
    end
end
```

Fifth Method

In still yet another embodiment, another method may be implemented which incorporates elements of both averaging and absolute-value processing. Set out below is illustrative Matlab code to implement the core concepts of one particular embodiment:

```
%Filter signal if directions diverge
Smoothecg=zeros(1,length(ecgin));
Smoothecg(1)=avgECG(1);Smoothecg(2)=avgECG(2);Smoothecg(3)=avgECG(3);
Smoothecg(end)=avgECG(end);Smoothecg(end-1)=avgECG(end-1);Smoothecg(end-
2)=avgECG(end-2);
for i=4:length(forwardECG)-3
    if abs(forwardECG(i) - reversECG(i)) <0.5*abs(avgECG(i)) || ...
            abs(forwardECG(i) - reversECG(i))<.05
        Smoothecg(i)=avgECG(1);
    else Smoothecg(i)=mean([Smoothecg(i-3) Smoothecg(i-2) Smoothecg(i-1)
avgECG(i) avgECG(i+1) avgECG(i+2) avgECG(i+3)]);
    end
end
```

Sixth Method

In yet still another embodiment, selective removal of impulse response artifacts is employed. In this embodiment, impulse response artifacts resulting from large amplitude peaks, such as QRS complexes, are selectively removed. The embodiment detects unusually large peaks in the filtered signal, then removes the impulse response that results from those peaks. Exactly when and how big the impulse response will be is known, so it is possible to remove at least some of it.

Note that it is undesirable to remove all of the impulse response effects from the entire signal because to do so would undo the effect of a comb filter. Accordingly, in this particular embodiment, only a few of the first peaks are removed (e.g., the first eight, for example) from the impulse response, to remove them only for signals with unusually large peaks. In addition, those peaks may be removed only after the filter has settled down after the start of compressions. Set out below is illustrative Matlab code to implement the core concepts of one particular embodiment:

```
function[ssECG]=iHoneycomb(ecgin)
%iHoneycomb
%
%Improved Honeycomb filter signal with selective impulse response
%subtraction
%
gain=204.918;%Gain of LP12 Paddles ECG.
sample_rate=125;%LP12 sample rate
ecgin=ecgin/gain;
%Manual entry coefficients for 1.67Hz filter at 125hz sample rate
b=[0.91 zeros(1,74) -0.91];%Normal coefficients
a=[1 zeros(1,74) -0.82067];%Normal coefficients (Q=16)
forwardECG=filter(b,a,ecgin);
%Selective subtraction of peaks. This seems to be an improvement over a
simple comb filter.
%Requires delay after start/stop of compressions
ssECG=forwardECG;
for i=sample_rate+1:length(ssECG)-sample_rate
    Th(i)=max([2*absmed(forwardECG(i-
round(0.5*sample_rate):i+round(0.5*sample_rate))) 0.07]);
end
for i=63:length(ssECG)-600
    if abs(ssECG(i))>Th(i) && i>1000 %Threshold and delay
        ssECG(i+75)=ssECG(i+75)+(.1619/.91)*ssECG(i);
        ssECG(i+150)=ssECG(i+150)+(.1327/.91)*ssECG(i);
        ssECG(i+225)=ssECG(i+225)+(.1086/.91)*ssECG(i);
        ssECG(i+300)=ssECG(i+300)+(.08892/.91)*ssECG(i);
        ssECG(i+375)=ssECG(i+375)+(.07275/.91)*ssECG(i);
        ssECG(i+450)=ssECG(i+450)+(.05947/.91)*ssECG(i);
        ssECG(i+525)=ssECG(i+525)+(.04858/.91)*ssECG(i);
```

```
        ssECG(i+600)=ssECG(i+600)+(.03964/.91)*ssECG(i);
    end
end
end
function[out]=absmed(in)
out=median(abs(in));
end
```

Figure 21:
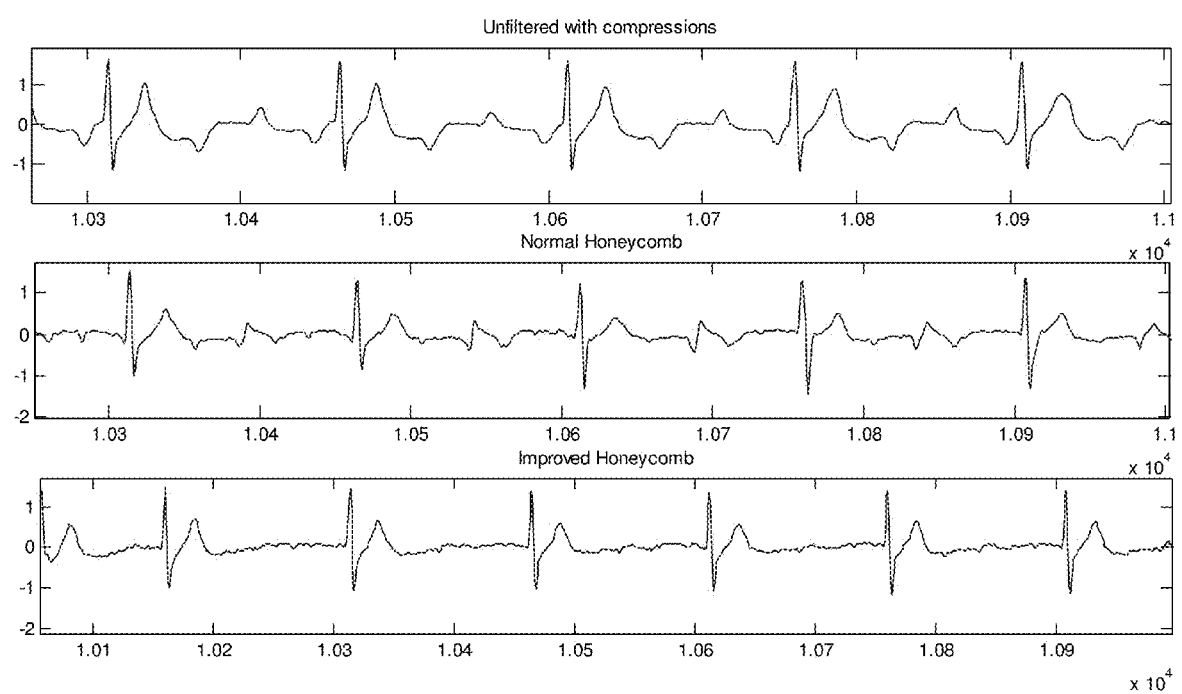
Figure 22:
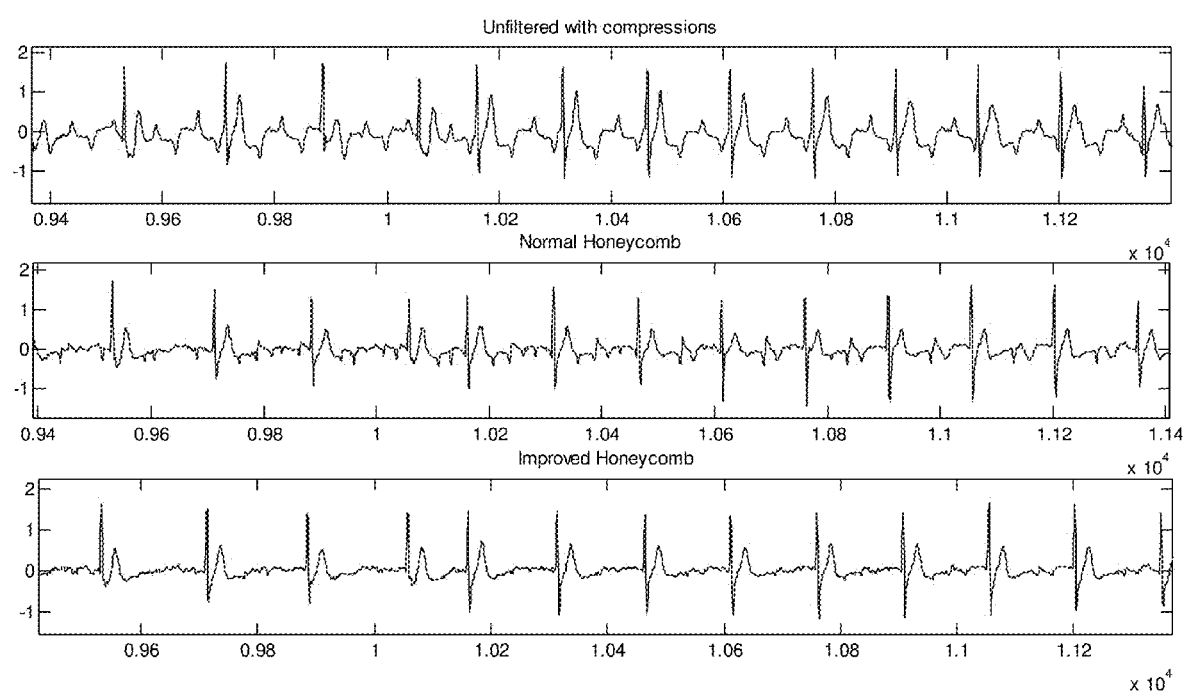
Figure 23:
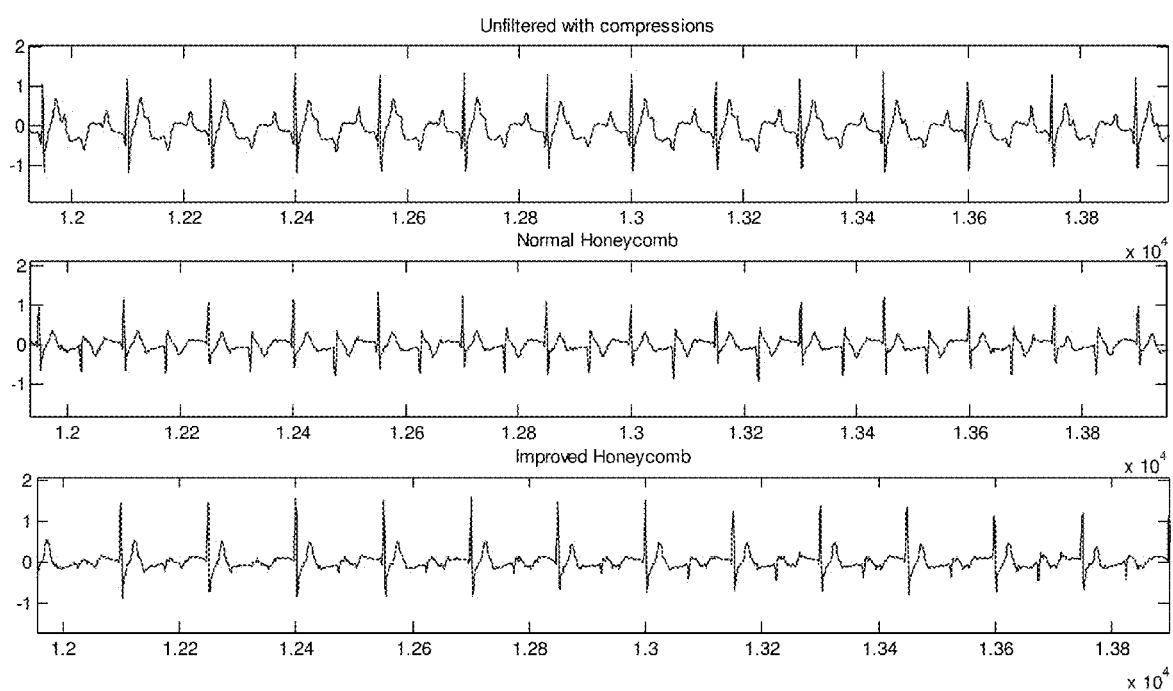
Figure 24:
FIG. 24 is another set of trace segments comparing one existing filter with another filter enhanced with embodiments based on the present disclosure.

FIGS. 21 to 23 illustrate examples of various traces implementing this particular embodiment. FIG. 24 is another set of trace segments comparing one existing filter with another filter enhanced with embodiments based on the present disclosure.

One of the advantages of the selective subtraction approach is that it can be implemented in a device for real-time device for real-time display. Other approaches, such as the averaging approach or the Weiner Filter, can only be done for post-processing.

Figure 25:
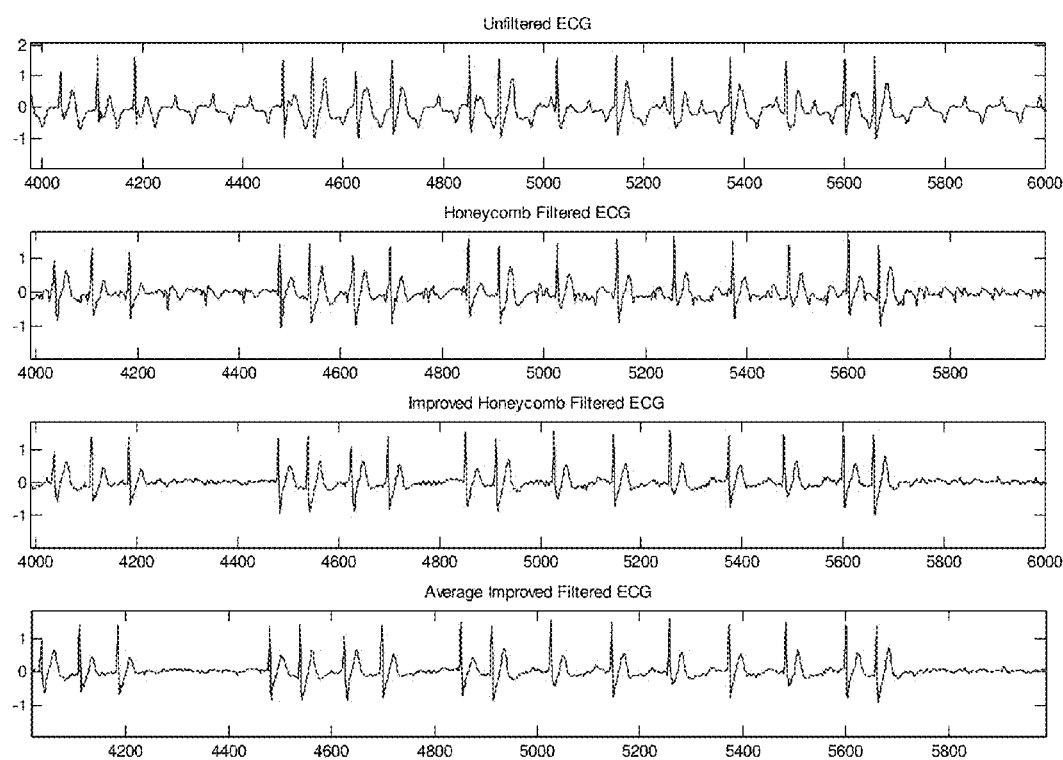
FIG. 25 is an example trace illustrating an embodiment that operates an improved comb filter with selective subtraction in the forward and reverse direction, then takes the average of the two filters.

It is also possible to run the improved comb filter with selective subtraction in the forward and reverse direction, then take the average of the two filters. FIG. 25 is an example trace illustrating that technique.

The improved comb filter with selective subtraction of impulse response artifacts appears to provide an improved filter over a conventional comb filter and could be implemented in a product with a real-time display. The improved filter with forward-reverse averaging provides a further improvement and could be implemented in Code-Stat.

In the foregoing description, numerous details have been set forth in order to provide a sufficient understanding of the described embodiments. In other instances, well-known features have been omitted or simplified to not unnecessarily obscure the description.

A person skilled in the art in view of this description will be able to practice the disclosed invention. The specific embodiments disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

What is claimed is:

1. A method for processing an ECG signal, comprising:
a port of an external defibrillator receiving the ECG signal including ECG data that represents QRS complexes of a patient, the ECG signal having a forward direction and a reverse direction, the forward direction representing the ECG data in temporal order, the reverse direction representing the ECG data in reverse temporal order;
a filter mechanism of the external defibrillator applying a filter to the ECG signal in the forward direction to create a forward-filtered ECG signal;
the filter mechanism applying the filter to the ECG signal in the reverse direction to create a reverse-filtered ECG signal; and
a processor of the external defibrillator combining a latter portion of the forward-filtered ECG signal with a temporally earlier portion of the reverse-filtered ECG signal to create a composite-filtered ECG signal, wherein the ECG signal further comprises impedance data that represents an impedance between at least two electrodes attached to the patient, and wherein the method further comprises:
the filter mechanism applying the filter to the ECG signal to remove compression artifacts that result from mechanical chest compressions delivered to the patent at a periodic rate;
the processor correlating the at least a portion of the impedance data with the ECG data; and
the processor analyzing the correlated ECG and impedance data to determine if the patient has return of spontaneous circulation.

2. The method recited in claim 1,
wherein applying a filter to the ECG signal in the forward direction includes the filter mechanism applying a comb filter to the ECG signal in the forward direction, and
wherein applying a filter to the ECG signal in the reverse direction includes the filter mechanism applying a comb filter to the ECG signal in the reverse direction.

3. The method recited in claim 1, wherein applying a filter to the ECG signal in the forward direction includes applying a non-adaptive filter to the ECG signal in the forward direction, and wherein applying a filter to the ECG signal in the reverse direction includes applying a non-adaptive filter to the ECG signal in the reverse direction.

4. The method recited in claim 1, wherein the port is an ECG port.

5. A method for processing an ECG signal, comprising:
a port of an external defibrillator receiving the ECG signal including ECG data that represents QRS complexes of a patient undergoing cardiac care, the cardiac care including mechanical chest compressions at periodic rate;
a filter mechanism of the external defibrillator applying a filter to the ECG signal to remove artifacts from the ECG signal related to the mechanical chest compressions; and
a processor of the external defibrillator selectively removing a predetermined number of impulse responses from the filtered ECG signal, the impulse responses resulting from applying the filter to the ECG signal.

6. The method recited in claim 5, wherein applying a filter to the ECG signal includes applying a comb filter to the ECG signal.

7. The method recited in claim 5, wherein applying a filter to the ECG signal includes applying a non-adaptive filter to the ECG signal.

8. The method recited in claim 5, further comprising:
the processor determining whether, for each portion of a plurality of portions of the ECG signal, the mechanical chest compressions are ongoing or stopped during the portion;
a display of the external defibrillator displaying the filtered ECG signal for each portion of the plurality of portions of the ECG signal for which the mechanical chest compressions are determined to be ongoing; and
the display displaying an unfiltered ECG signal for each portion of the plurality of portions of the ECG signal for which the mechanical chest compressions are determined to be stopped.

9. The method recited in claim 5, wherein selectively removing a predetermined number of impulse responses from the filtered ECG signal further includes:
the processor calculating a median of an absolute value of the filtered ECG signal over a window;

the processor identifying each data point in the filtered ECG signal that exceed two times the calculated median; and the processor removing a predetermined number of the identified data points.

10. The method recited in claim 9, wherein removing a predetermined number of the identified data points is removing a first eight of the identified data points.

11. The method recited in claim 9, wherein displaying the filtered ECG signal is displaying the filtered ECG signal in real time, and wherein displaying an unfiltered ECG signal is displaying an unfiltered ECG signal in real time.

12. The method recited in claim 5, wherein the port is an ECG port.

* * * * *